(12) United States Patent
Howard et al.

(10) Patent No.: US 7,384,772 B2
(45) Date of Patent: Jun. 10, 2008

(54) CHITIN DEGRADATIVE SYSTEMS

(75) Inventors: Michael Howard, Annapolis, MD (US); Steven Wayne Hutcheson, Columbia, MD (US); Ronald M. Weiner, Potomac, MD (US)

(73) Assignee: The University of Maryland, College Park, MD (US)

( * ) Notice: Subject to any disclaimer, the term of this patent is extended or adjusted under 35 U.S.C. 154(b) by 274 days.

(21) Appl. No.: 10/875,518

(22) Filed: Jun. 25, 2004

(65) Prior Publication Data

US 2005/0112750 A1    May 26, 2005

Related U.S. Application Data

(60) Provisional application No. 60/483,135, filed on Jun. 27, 2003, provisional application No. 60/483,383, filed on Jun. 27, 2003.

(51) Int. Cl.
*C12N 9/26* (2006.01)

(52) U.S. Cl. ..................................... 435/200

(58) Field of Classification Search ................. 435/201
See application file for complete search history.

(56) References Cited

OTHER PUBLICATIONS

Zhu Z. et al. Acidic Mammalian Chitinase in Asthmatic Th2 Inflammation and IL-13 Pathway Activation, Science 2004, 304, 1678-1682.*
Wills-Karp M. et al. Chitin Checking—Novel Insites into Asthma, New Eng. J. Med., 2004, 351, 1455-1457.*
Bierbaum S. et al. Polymorphisms and Haploides of Acid Mammalin Chitinase Are Associated with Bronchial Athma, Am. J. Respir. Crit. Care Med. 2005, 172, 1505-1509.*

* cited by examiner

*Primary Examiner*—Rebecca E. Prouty
*Assistant Examiner*—Malgorzata A. Walicka
(74) *Attorney, Agent, or Firm*—Arent Fox LLP

(57) ABSTRACT

The present invention relates to chitin degradative systems, in particular to systems containing enzymes that bind to and depolymerize chitin. These systems have a number of applications. The present invention also describes enzymes with at least two catalytic domains in which the domains are separated by poly-amino acid linkers.

4 Claims, 3 Drawing Sheets

SEQUENCE LISTING

<160> NUMBER OF SEQ ID NOS: 22

<210> SEQ ID NO 1
<211> LENGTH: 543
<212> TYPE: PRT
<213> ORGANISM: Microbulbifer degradans

<400> SEQUENCE: 1

```
Met Phe Lys Lys Thr Leu Ala Val Ala Gly Leu Ala Leu Ala Ala Asn
  1               5                  10                  15

Asn Ala Phe Ala Ala Thr Asn Cys Ser Asp Leu Thr Asp Trp Asn Ser
                 20                  25                  30

Ser Thr Ala Tyr Thr Gly Gly Thr Ser Val Lys His Ala Asn Ser Lys
             35                  40                  45

Tyr Thr Ala Gln Trp Trp Thr Gln Gly Ala Asp Pro Thr Ser His Ser
         50                  55                  60

Gly Gln Trp Gln Glu Trp Lys Phe Ile Asp Gln Cys Ser Ser Ser Ser
 65                  70                  75                  80

Ser Ser Ser Ser Ser Ser Ser Ser Ser Ser Ser Ser Ser Ser Ser Ser
                 85                  90                  95

Ser Ser Ser Ser Ser Ser Ser Ser Ser Ser Ser Thr Ser Ser Ser Ser
                100                 105                 110

Ser Ser Ser Ser Ser Ser Ser Gly Gly Ser Cys Thr Asp Ala Pro Val
            115                 120                 125

Phe Ala Glu Asn Thr Ala Tyr Asn Thr Gly Asp Val Val Thr Asn Leu
        130                 135                 140

Glu Asn Leu Tyr Ser Cys Val Val Pro Gly Trp Cys Lys Leu Gly Gly
145                 150                 155                 160

Ala Tyr Glu Pro Gly Gln Gly Trp Ala Trp Glu His Ala Trp Asn His
                165                 170                 175

Val Gly Thr Cys Gly Thr Ser Ser Ser Ser Ser Ser Ser Ser Ser Thr
                180                 185                 190

Ser Ser Ser Ser Ser Ser Ser Ser Ser Ser Ser Ser Ser Ser Ser Ser
            195                 200                 205

Ser Ser Ser Ser Ser Ser Gly Gly Val Gly Gly Lys Val Pro Ala
        210                 215                 220

His Ser Leu Val Gly Tyr Trp His Asn Phe Val Asn Gly Ala Gly Cys
225                 230                 235                 240

Pro Met Arg Leu Ser Glu Met Ser Asp Lys Trp Asp Val Ile Asp Ile
                245                 250                 255
```

```
Ala Phe Ala Asp Asn Asp Pro Ala Ser Asn Gly Thr Val His Phe Asn
            260                 265                 270

Leu Phe Pro Gly Thr Gly Asn Cys Pro Ala Met Asn Ala Glu Gln Phe
        275                 280                 285

Lys Ala Asp Met Arg Ala Leu Gln Ala Gln Gly Lys Val Phe Val Leu
    290                 295                 300

Ser Leu Gly Gly Ala Glu Gly Thr Ile Thr Leu Asn Thr Asp Ala Asp
305                 310                 315                 320

Glu Val Asn Phe Val Asn Ser Leu Thr Asn Leu Ile Asn Glu Trp Gly
                325                 330                 335

Phe Asp Gly Val Asp Ile Asp Leu Glu Ser Gly Ser Gln Leu Leu His
            340                 345                 350

Gly Ser Gln Ile Gln Ala Arg Leu Ile Thr Ser Leu Arg Thr Ile Asp
        355                 360                 365

Ala Asn Val Gly Gly Met Val Leu Thr Met Ala Pro Glu His Pro Tyr
    370                 375                 380

Val Gln Gly Gly Tyr Ile Ala Tyr Ser Gly Ile Trp Gly Ala Tyr Leu
385                 390                 395                 400

Pro Ile Ile Asp Ala Leu Arg Asp Gln Leu Asp Leu Leu His Val Gln
                405                 410                 415

Leu Tyr Asn Asn Gly Gly Ile Leu Ser Pro Tyr Asn Pro Gln Thr Phe
            420                 425                 430

Pro Ala Gly Ser Val Asp Met Met Val Ala Ser Ala Arg Met Leu Ile
        435                 440                 445

Glu Gly Phe Asn Thr Gly Asp Gly Gly Tyr Phe Gln Gly Leu Arg Pro
    450                 455                 460

Asp Gln Val Ser Leu Gly Leu Pro Ser Gly Pro Ser Ser Ala Gly Ser
465                 470                 475                 480

Gly Leu Ala Thr Asn Gln Ala Ile Met Asp Ala Leu Asp Cys Ile Thr
                485                 490                 495

Arg Gly Thr His Cys Gly Thr Ile Asp Ala Gly Gly Ile Tyr Pro Ser
            500                 505                 510

Phe Asn Gly Val Met Thr Trp Ser Ile Asn Trp Asp Ala His Asp Gly
        515                 520                 525

Tyr Ile Phe Ser Asn Pro Ile Gly Asp Lys Val His Ser Leu Pro
    530                 535                 540

<210> SEQ ID NO 2
<211> LENGTH: 3816
<212> TYPE: DNA
<213> ORGANISM: Microbulbifer degradans

<400> SEQUENCE: 2
atgaatttaa ctaaatttgc agtggctgca cttagtgttg ccgtactttc tgcatgtggc      60
ggaggcgccg gtaacagccc tagccccggt gcaggttcca atacaaatac tgagtcggca     120
tctagcagct ccagttccag ctctagttct agcacaagtt caacatccag ttcttcttcc     180
agctctagtg gttcagcaga agtaaatgta gatattgacg ttgatatcga gtgtggaaaac    240 ggctctagtt cgagcagctc atcaggctct agctcgtcta gcacgggcgg tggcgatatt    300
actattattg acgaaataga gagctcgacc agttcttcta cgtctagctc aagttccagt    360
ggcgcaacaa gttcaagcag tacttcttcg tctagcagtt cttcaagcag ctctagttca    420
tctggcgcta ccggctcgtc atctagcagc tctggtgcgg gtagtactag ttcatcatca    480
agctctagta gctcaagttc gtcttctagt tcatcgtcaa gttcttcaag ctcttctagt    540
```

```
tcatcaagca cgggcggtgg caatgcgggt gtagatgccg aattgggtta cagcattggc      600
gacgtctatg cgccaagctt tgattacacc gcagtaggcg gcgagcgcaa aacagataac      660
taccgcgtta ttggctatta catgccaagt ttagatggtt cgtttccgcc tagcgcaatt      720
ggtgagcaac aagcgcaaat gcttacccat attaactatg catttattgg tattaacagc      780
cagctagagt gcgattttat agatgtagaa aaagccgacg cagaaactca aattattgct      840
gagttacaag cactaaaaaa ttggaatgcc gatttaaaaa tccttttttc tgtaggggt       900 tgggcagaat ctaacgacgc agccgaaacc gttagccgct accgcgatgc gtttgcaccg      960
gcaaaccgcg agcattttgt tagctcgtgt gtagccttta tgcaacaaca cggctttgat     1020
ggcatagata tagattggga ataccctcgc gccgaagatg tagataactt tattgccggc     1080
ctagcagcaa tgcgcaacca attggatgca cgcggcaacg gcgagctagt taccattgct     1140
ggcgcaggcg gtgcgttctt tttaagccgt tattacagca agctagctgc catagtagaa     1200
cagttagact ttataaattt aatgacctac gacctaaacg gaccgtggaa cggcgtaaca     1260
aaaactaact ttcacgcaca cctgtacggc aacaaccaag agccgcgctt ttacaacgcg     1320
ctgcgcgaag cagaccttgg tttaacgtgg gaagaaatag tagagcgttt tcctagcccg     1380
ttcgagctca ccgtagatgc cgccattaaa caacatttaa tgatggatat tccgcgcgaa     1440
aaaattgtaa tgggcgtacc tttttacggt cgtgcatttt ttaacacagg ttcatcaaac     1500
accggtttat accaaacctt taacaccccca aatggtgacc cctatgtagg tgacgctagc     1560
ttattggttg gttgtgaagc ctgcgaagcg cgcggcgagc cacgcattgc tacctttaac     1620
gatattcaac aacttataga aggtaactac ggctataccc gtcactttga tgatcaaacc     1680
aaagcgcctt ggttgtatca cgcagaaaat aatatatttg taacctacga cgatgctcaa     1740
tcgttggtgt ataaaaccga ttatattaaa caacaaggtt taggcggtgc gatgttttgg     1800
cacctaggcc aagatgattc gcaatttact ttattggcta ctttacacac cgagctaaac     1860
ggcgcaaacg ctggtagcct gcaaggtggc aatagcgaaa ccgacaacac aacggacgaa     1920
acagaaggca ataacgaaga caacaccgaa caaaacccag aagaaaatac cgatactgaa     1980
gaaacagaaa cagaaacaga aacagaaaca gaaacagaaa cagaaacaga aacagaaaca     2040
agcgtagagc aacccactgc gccaacaata gcttggatga acacaagcta taccggcagc     2100
agtgtaacgg tcactattac gtggaatatg tactggggta caaacggcaa ccaatggcag     2160
ctatggttag atggcgagca agtgtattca gccaacttaa ctaccaatgg ccaaaatgca     2220
caaaccgaca gcaaaatcat tactattact ggcgcaggtg ctcatagcgt tgaagttaaa     2280
ctgtgtaacc agcaagatat aaatgttagc tgtgctagcg atagcgaaac tatcactttg     2340
caaggcggta gtgatggcgc aacgtctagt tcttcttcca gcacgtcgtc aagctctagt     2400
agctcgtctt ctagtactgg tggttcaacg tcgagcacaa gcagctcctc tagttctact     2460
agttcatcga gcagttcatc tagctctagt agttcaagta catcgggtgg cggcgaaaca     2520
gatttatctg gcgtggttta cggcgagtac aacaacactt acaaacagac gagcgataaa     2580
ataattgtta cttactttgt agagtggggc atttatggcc gcgactatca cgtaaataat     2640
attccggcgt ctaaccttac gcacgtactg tttggcttta ttgcaatgtg tggcgataac     2700
ccacacgcct caggcggcgc gcaagcggct attgctagcg agtgtgcaga taagcaagat     2760
tttgaagtta ccttggtaga tcgtttcgcc aacctagaaa aaacttaccc aggcgataag     2820
tggtacgacg atacaaccgg tcaagattac aatggtaact ttgggcaact acgcaaacta     2880
```

-continued

| | |
|---|---|
| aaagcacagc acccgcattt aaaaatattg ccatctattg gcggctggac aatgtctacc | 2940 |
| ccattttatg aaatggcaaa aaatgaagct aaccgcgcag tgtttgttga atctgccgtt | 3000 |
| aactttatta aaaaatatga cttcttcgac ggagtagata tagattggga ataccctgta | 3060 |
| tacggcggta cagccccaga attatctacc gctgccgacc gcgatgccta taccgcctta | 3120 |
| atgcgtgacc tacgcgcagc attagacgag ctggcagaag aaacgggtcg cgaatacgaa | 3180 |
| attacttcgg ccgtaggtgc agcaccgaaa aaaattgcag cagtagatta cgccagtgcc | 3240 |
| acaacgtata tggattacat attcctaatg agctacgact acatgggcgc atgggcgaac | 3300 |
| acaacgggtc accacacccc gctgtacaac aacaacgaag agcgagaagg ttttaacaca | 3360 |
| catgcgtctg tgcaaaacct attaaccgca ggtgtgcctt catccaaatt agtcgtgggt | 3420 |
| ggtgcattct acggccgcgg ctgggtaggc acccaaaata ccaacgctgc caaaagcgat | 3480 |
| ttattcccgc tatatggcca agcttctggc gcggcaaaag gcacctggga agcaggggta | 3540 |
| caagactacc gcgacctgta cgacaactat attggcacca atggcacagg cattaatggc | 3600 |
| tttagcgcac actacgacga aatagccgaa gccgcctacc tttggaacag cagcaccggc | 3660 |
| gaatttataa gctacgattc gccgcgctct attgcagcaa aagccgatta cgtaaaacaa | 3720 |
| tacaatctag ctggcatgct aacctgggaa atagacggcg ataacggcca actactcaac | 3780 |
| gccattaacg aaagtttcgg caacgaaaag cagtag | 3816 |

<210> SEQ ID NO 3
<211> LENGTH: 2379
<212> TYPE: DNA
<213> ORGANISM: Microbulbifer degradans

<400> SEQUENCE: 3

| | |
|---|---|
| atgaacccta tagctaaaact cacattagcc actggcgcca tgctaagtgc gcatgtggcc | 60 |
| tacgcttacg actgcgatgg ccttgccaca tggaacgcat cgtctgccta tgccggctct | 120 |
| accgttgtgc aacacagtaa cgtggcttac aaagccaact ggtggacaca aaaccaaaac | 180 |
| cccgcttcac attctggccc ttggcaagag tggacgaacc taggcaactg cgatggcgac | 240 |
| ggtggcggca acaccaacca agcgcccagc gcaaatgcca acggcccta cgccgcgcaa | 300 |
| cttggcgccg ccatagcgtt tagctctgca ggctctagcg atagcgacgg caatattgcc | 360 |
| agctacaact ggacctttgg cgacggtaac agcagcaacc aagctagccc aagccacacc | 420 |
| tatggcagcc aaggcaccta cgcggttacc ttaaccgtta ccgataacga aggcgcaagc | 480 |
| agcagtgcca ccacaagcgc aagcgttacc caaggcggag accctggcga ttgccaagca | 540 |
| ccgcaataca gtgcgggcac ccaatacgct gcgggcgata tcgttgccaa tggcggcaac | 600 |
| ctgtaccagt gtaatattgc gggctggtgc tcttcatctg ccgcatgggc ctatgcccca | 660 |
| ggtactggcg cacactggca agatgcgtgg tcacttacga gcgaatgcga cgacaacggc | 720 |
| aacaccaacc aagcacctac agccaatgct aacggcccat attctggtag cgctggtata | 780 |
| agcattagtt ttagcagcaa tggctctgcc gacagcgacg gcacaattgc cagttacagt | 840 |
| tggaactttg gcgacggcgc aagcagcagc caagcaaacc caagccacag ctacatgaat | 900 |
| gaaggcactt accaagttag cctaaccgta accgatgacg acggcgcgag cgccaccgca | 960 |
| ttcaccaccg ctaacgtaac tggtaatggc gaaaaccaag agcctgttgc aagcattagt | 1020 |
| gcaccatcca gcgctagcga aggcgctagt gtgaactttt ccagcgcggg cagtaacgac | 1080 |
| ccagacggca gcatagttag ctacagctgg aactttggcg atggcactag cagtcaacaa | 1140 |
| gctaacccca gccacaccta cagcagcgca ggtagctata gcgttagcct aacggttgtt | 1200 |

```
gataacgaag gcgcgaataa cgtcgccaac cacagcatta caatcagtgg cgataccggc   1260
ggcggtacac acggcgataa aattattggc tacttcgcag agtggggcgt atacggccgc   1320
aattatcacg ttaaaaacat tcacaccagc ggctctgccg acaaactcac tcacatcgtt   1380
tacgcgtttg caacgttca aaacggcgag tgtaaaattg gcgattccta cgcagcatac   1440
gacaaagcct acagcgcagc agacagtgta gatggcgttg ccgatacttg ggacgacggt   1500
gtactgcgcg gtaacttcgg tcaactacgc cgcttaaaag ccatgcaccc acaaattaaa   1560
atagtgtggc ctttcggtgg ctggacatgg tctggcggtt ttggcgaagc agcagcgaat   1620
gccgatcact ttgccaactc ctgttacgac ttagtattcg acgcacgctg ggcagacgtt   1680
ttcgacggca tcgacatcga ctgggaatac cccaacgact gcggcctaag ctgtgataat   1740
agcggctacg atggctaccg cgtactcatg caagcattgc gcaatcgttt tggcaacaaa   1800
ctagtaaccg ctgccattgg cgctggcgaa tctaaacaaa atgcagccga ctacggtggc   1860
gcagcacagt acttagattt ttacatgcta atgacctacg acttcttcgg cgcatttaac   1920
ccacaagggc caaccgcacc gcactccacg ctataccaact acccaggcat gccaatagaa   1980
ggattctctt ctgaccacgg tatccaagta cttaaaagca aggtgtacc tgccgagaaa   2040 atcttactgg gcataggctt ttacggccgc ggctggacca acgtaacgca agatgcccca   2100
ggcggcagcg ctaacggcgc agcacctggc acctacgaaa aaggcattga agattacaaa   2160
gtgttgaaaa acacctgccc agccaccggc acaattgccg gcaccgctta cgccaaatgc   2220
ggaagcaact ggtggggcta cgacacacca gccaccatcg atagcaaaat ggactacgcc   2280
aaacaacaag gcctaggcgg cgcgttcttc tgggagctaa gtggcgacac caccgatggc   2340
gaactgatta gagcgattga taatggctta aaaaactaa                          2379

<210> SEQ ID NO 4
<211> LENGTH: 1347
<212> TYPE: DNA
<213> ORGANISM: Microbulbifer degradans

<400> SEQUENCE: 4
ttgcaaccga taaatcaac taaaaggaac ctaatcatgt tcgcaaagaa aattacatac      60
tccactatag ccttggccat cgcagggctt tctggtaacg cactatctca cggcttaatg    120
gtagacccgc cttcgcgtaa cgcgctgtgt gggatgatag aaaaacctga ccaagcaaca    180
tcacccgcct gccagcaagc tttccaaaat gactttaatg cggctacca atttatgagc    240 gtgctaaccc acgacatagg tcgccaaggc ggcacgtcta ataatgtgtg tggctttgat    300
agcgaaacct ggaatggcgg tgcaaccccg tgggatgccg caattgattg gccaaccact    360
caaattagtt ctggcccgtt agaaatagat tggaatattt cttggggccc tcactgggac    420
gacaccgaag agtttgttta ctacattacc aagcctgact ttgtatacca ggtaggtgta    480
ccgctcagct ggagcgattt cgaggcaaca ccttttttgcc aactcgacta cagcgatgca    540
aacccaaacg caaaccctgg cgtatccacc accaaaagtg ccaacctatt tcacactcaa    600
tgtaacgtac ctgcgcgctc tggccgccac gtgatttacg gtgaatgggg cgcaactac    660 tttacctacg agcgattcca cggctgtatg gatgttacct ttggcggtag caacccaccc    720
cctagcaacc aagcgccaac agctaacgct caatctgtaa atgtaagtag cggtagcagt    780
gtctctatta ccttaagcgg cagcgatgta gatggtgtta ttagcagtta cgcaattgca    840
gcagcaccta gtaacggaag tttaagcggg tctggcgcgc agcgtttata cacacctaat    900
```

-continued

| | |
|---|---|
| ggcaatttct cggggttcgga tagcttccaa ttcacagtaa ccgatgatga cggagcaaca | 960 |
| tccaatgccg cgaccgttag cattaatgta agctctcaac cagaaccaga acccgaaccc | 1020 |
| gagccagaac cagagcccga accaggaact ggcgctagct gtgagcacgt tgttgtaaat | 1080 |
| gcttgggata gtggcttcca aggcgctatt cgcataacta acactagcga ccaaaatatt | 1140 |
| aacggctgga atgtaagctg gagctacaac aatggcacta caattagcca gttgtggaat | 1200 |
| gcaaacttct cgggcagcaa cccttacagc gcaagcaacc taggttggaa cgcaaccatt | 1260 |
| caaccaggcc aaactgttga atttgggttt accggtaacg gctctgtacc cgcggcacca | 1320 |
| gcagtaacgg gtgcggtttg taattag | 1347 |

<210> SEQ ID NO 5
<211> LENGTH: 3441
<212> TYPE: DNA
<213> ORGANISM: Microbulbifer degradans

<400> SEQUENCE: 5

| | |
|---|---|
| atgaaaaata agcactgcct agccgctttg gcgctggcga tttctaccca tgcgtatgcc | 60 |
| gcacctggca cgcccaatat tgcgtggctg cccgctaccc acgaaagtgg cgaagccata | 120 |
| aacgtacatt gggatatgtg gtggggtgaa acggcaccg agtggcaatt aaccgataac | 180 |
| ggcgacctgc gctgcagcgg cagcctaaca gccaacggcc aaaaccaaca aagcgcggaa | 240 |
| tgcgccgcta actacagcag cggcagccat gcactgcagg ttagcttgtg taataccagc | 300 |
| ggctgtagcg aaagtaatgt tgttactatt aacgttaacc aaggcgcaag tagcaacgtg | 360 |
| ccacctcaag tatccattag cgcaccggca agtgcagggg aggggactc gataacccctt | 420 |
| agcgctacgg ccagcgacag cgacggcacg attacctctg taaccttttt agtcgatggt | 480 |
| attgccatag ctaccgatac caccagccca tacagcacaa actggatagc gaaagcgggt | 540 |
| actcactcac ttaccgcgca agcgctagat aaccaaaatg ccacaggcga tgattctgta | 600 |
| agtattagcg ttaccagcgc ccctaaccaa ttgcccagcg tgagcttggt tgctcccaat | 660 |
| gcaaacttaa tggcgggcag cgagaccagc tttgaaataa cgctagcga cgccggtggc | 720 |
| agtattagca gtgttgaatt gtacttaaac ggcaatttac tcggcaccga taccagcgcg | 780 |
| ccttacaacg ttagctggac agcagaagcg ggcgatcaca gcatttacgc cgtagcaagc | 840 |
| gacgatcgcg gcggtgtgag tcaatcggac acggtatttt taaccgtagc ggaagacaca | 900 |
| aatgcagcgc ctagcgtaag cctttcaacc gtaccaacag cgcaatgga aggtgatgca | 960 |
| ctcacacttg aggcagcagc aagcgacagc gatggcagtg ttgcgcaggt ggacttttac | 1020 |
| ctaaacaacc aactactagg cagcgccaca agcgcaccct acagtttgca atggacagcc | 1080 |
| acgcgcggca gccacacctt gcgcgcaacc gctgtggata ccaaggtaa acagccagc | 1140 |
| gcgattagca cctttagcgt tgctgcagac acaagcgcca gccacgaaga ctgccgacca | 1200 |
| gacgggcttt acgccacgcc agaagtgcaa tcgccttact gtactgttta cgacatacaa | 1260 |
| ggccgcgagc taatgggcag cgcaacgcgc cgcgtgattg gttacttcac tagctggcgt | 1320 |
| actggtggta acgccccggc ctaccttgca caccaaattc cctgggacaa gctaacccac | 1380 |
| attaactacg cctttgccca tgtggatggc aacaaccacg tttcaattgg cgccaatacc | 1440 |
| ccaaccaatg cagcaacggg tatggaatgg ccagacgtag ccggtgccga aatggaccca | 1500 |
| agctttagtt acaaaggcca cttcaacctg cttaacaaat acaaaaagca gtacccacac | 1560 |
| gttaaaacgc ttatctctat tggcggttgg gcagaaacag gcggctactt tgatagcaat | 1620 |
| ggcgaccgcg taaattctgg cggcttctac accatgacca ccaatgcaga cggttcggtt | 1680 |

-continued

```
aacaccgccg gtatcaacac ctttgccgac tcggtagtgg agtttttacg cacctacagc   1740
tttgatggcg cagatataga ttacgaatac cccacatcga tgaacgatgc cggcaaccct   1800
tcagatttcg ccatcgccaa tgcgcgtcga aaaggcttaa acgcttcgta caacgtgttg   1860
atgaaaaccc tgcgccaaaa gctggatata gcagggagc aagatggcaa gcactacatg    1920
cttaccatcg cctcgccatc gtcaggctat ttgttgcgcg catggaagc atttgaagca    1980 acccagtact tggactacgt caatatcatg tcctacgact tacacggtgc atggaaccag   2040
tttgtaggcc ccaatgcggc actgtttgat aacggccaag atgcagagct tattcagtgg   2100
aacgcttacg gcggccagta caaaaatatt ggctacctca acaccgactg gcttaccac    2160 tacttccgcg cgccatgcc ggcgggccgc attaacattg gtgtaccta ctacacccgc    2220 ggctggcagg gcgtaaccgg tggcaccaac ggtttatggg gccaagcatc cctgccaaat   2280
caaagcgaat gccctgtggg taccggcggc agcgccacca gtaaatgcgg caacggcgcg   2340
gtgggtatag ataacctatg gcacgacaag gatgaaaacg gcaacgaaat gggcgcgggt   2400
tctaatccca tgtggcacgc taaaaaccta gaaaacaata ttctagggga ttacctaaca   2460
gcctacggct tagacccaat caacaaccca gatcaccaac ttagcggtaa ctaccagcgt   2520
tattacgacg atgtattagt cgccccgtgg ttgtggaacg ccgctaagca ggtatttatc   2580
tctaccgaag acgagcaatc catcaaccgc aaagccgatt acgtagtaga aaacggcata   2640
ggcggcatta tgtttttggga actagccggc gattaccaat tcaatgcggc caagggccaa   2700
tacgaaatgg ccacacgct aaccaccgcc attgcagata aatttgccaa cgcgccagcc    2760
tacggcaacc agcgtgcaga aattgatatg ccccagcaaa cgttagatat aggcataaag   2820
ctaactaact ttgccttggg tgataacaac ttccccatta cgccagacct aataattact   2880
aacaacacag gccaaaactt gcccggcggc accgagttct atttcgatat cgccacctct   2940
accccagata catgggcga ccaaagcgca gcgagcttaa ccattgttag caacgggtct    3000
aacgcggcgg gtaacaatgt gggcggttta gaaaacaact tccaccgcgt aaaaataagc   3060
accccaagct acctcaccct tgccgacggc gaagaatgga agtagtact taaatactac   3120 ctaccagttt ctatgccttc taactgggtg gttaacgtag ctggcgaaga gtttgcgctt   3180
agcagcgagt accctaactt gccgatgggc agcattagtt ctggtggcgg caataacggc   3240
ggtggcaaca ccggtggcga ttgcagcaac gcaagcgact acccagctta ccctaacttt   3300
ccacaaaaag actgggccgg aaaccccagc cacgccaacg ccggtgaccg catgacccac   3360
aacaacgcgc tgtatgaagc caaatggtgg acaagtgcaa ccccaggtac atccgattgg   3420
gacttggtat gtacgtttta a                                            3441
```

<210> SEQ ID NO 6
<211> LENGTH: 2388
<212> TYPE: DNA
<213> ORGANISM: Microbulbifer degradans

<400> SEQUENCE: 6

```
atgaaactaa gattattacc acatagtata agtttagcat cgctattact gctaagtgct    60
tgccagcaag agcacgcaac cagtacaaac gcgcaactct cccctattgc accgcctgct   120
atctctattg ttcccgcacc ggtttcggca gaaataaaaa cagggcagtt tgtttttggt   180
aatagcacac agcttacagt taacagcgaa aagctaagag atgttgcgca gctttgggcg   240 gatttttta atgttgctag tggtattaat ttacaggttc aaagcgctac aggtaatagc    300
```

```
gatgaagcaa atagcgtaag tcttgagttg gtgccggctt cagaattctc atcaagcaat      360
gcagaagcct atgaattaac ggttacagat aatgcaataa cagtacgcgc tagcactcgc      420
gcgggtattt tttacggctt aaccagtttg cgccagttat tgccgccgca aatagaatca      480
ccctccccta ttaattctgt aaattgggtt gtacctgcgg ttgctattgt cgacgagccc      540 ttataccccct atcgcggtat gcacttagat gtaagccgcc acttttcga tgtgaatttt      600 attaaacgct atatagatat attagcgttc acaaaatga atcgtttcca ttggcattta      660
accgatgacc aaggctggcg tattccgatc gacgcctacc ccctactcac agaaaaatcg      720
gcttggcgag acaaaacggt tataggccat acctacgacc gcgacgtagc ttacaacact      780
aatagaatag gcggttttta tagcaaagaa caaatacgag acatagttgc ttacgctgca      840
gaacgccaaa ttatggtaat tccagaaata gatgtccccg gccacgcagc agctatttta      900
cacgcttacc cagagtttgg ttgtatcgag caagtttcac aggtgcaaag caactttggc      960
attttcgagc aagtgctttg cccaaccgag ccaacccttg aattttttgcg cgcagtgttt     1020 accgaagttg ccgagttatt ccctggcgaa tacctacatg taggtggcga cgaagtaaaa     1080
aaagttcagt ggcaacagtc acccttttgtt accgaattaa tgcagcgtga aggtttaaaa     1140
gactaccacg aagtacagag ctactttatt tgccgcgtag gcgagatagt aagtagctta     1200
gataaaaaaa tgttgggctg gaacgaaata ctcgacgggg gtattgctcc caatgcgact     1260
attatgtctt ggcaaggtgt tgaaggtggt attgctgccg ccgagctggg ccacgatgcg     1320
attatgtcgc cgggaaacta tgtgtacttc gatcactttc agtctcgctc ggtggatgaa     1380
ccacttgcca ttcacggtat tacaccgtta tcagaaacat actcttacaa ccccatgccc     1440
gaacaatttg ctggcacaga aaagccaag cacatactcg cgcccaagg gcaactgtgg       1500 acagagtacg tgcctaccac agcaaaagcg gagtatatga tactgccaag attaagtgcg     1560
gtagcagaaa taacctggac accagtcaac aagcaatcgt ggcaaagctt tagcgaaagg     1620
ctacccagcc tatttgcccg cttttgacgaa atgggcttaa acgcagcgcg atctgtttat     1680
gcaattaccg ctaccgcaaa aacggaaggc agcggtgaag atgccaaata ccgcgtaaac     1740
cttgcctccg atacggctca tgtaattatt cgctacacaa ccgacggcac cttgccgaat     1800
gcgcaatcgc ctatttatag cgaaccattt ttagtagaag gcgatacgtt tgtgagggcg     1860
cgtagccaag ataaaataag tggtaacttc tacctggaat cgcaactgcg caccgtaaaa     1920
cacaaagccg ttggcgccaa gctaacactg ttaagcgaag cgaatacaga gtggaataaa     1980
gacccagtaa aaaccttaag tgatggcatt acttcgatag accaaatatt tcaactcgac     2040
gactgggcca cattttttgg cgacgaggtt gttgcacata taaccttcgc taaggcacaa     2100
accgttagcg aagtaagcat tggctttaac cctggcaagc atcgccaaat gtacccaccc     2160
actcgtttgc atattttaag ctcaagcgat ggcgaaacat ggcaaagctt gggtgaagcc     2220
gacccacaac accttgccac cgcaaaaaat cgcgtaagtt acacctttgc accaacaacc     2280
actcgccacc tacggataga ggcggaaaat aaaacccgcg tactaagtac cgaaagcggt     2340
aagctaaaaa gcgttcccct atacttagat gaaataatcg ttaaataa                 2388

<210> SEQ ID NO 7
<211> LENGTH: 2670
<212> TYPE: DNA
<213> ORGANISM: Microbulbifer degradans

<400> SEQUENCE: 7
atggcgttat ttagcaagta tgtatggcaa gtggcagttg ccggagcatt aggtacggtt       60
```

-continued

```
agtttgctgg gtagtcgttt atacgcgcaa actgcagata cacagcaatg gattgatggc    120
atagccagca atatgcaggt gcattatcaa gtactgctaa ataagggtga cggcgaatgc    180
agcttgccaa gcttaccgcc cagccccaaa tcaccatgct ctatagttga gctttcactc    240
agctcgccag ataagcttgc ggcaaacgac ttagatggta actggtctat ttacttcagc    300
caaaccgatc ccatttatgc gcacccagct ggtgaattta caatcgacca tataaatggc    360
gatttacacc gaattcgccc cagcgccagc taccaaggat ttaatgtggg cgaagttaaa    420
aaggtgcagt ttattgtggc gggtttaacc cttaccgaag ccaaaataat gcccaactat    480
tatgtggtag cagaagggca agataataaa caggcactat acagcgaagc ccgtgttatc    540
gaatcaacac gtattcgtat acacccagaa acagggttag aggagcgacc ttttgcaggc    600
gaaataagta ggcaaaattt taagctgtcg caggcagata aaacgcctta cgccgatgcc    660
gcttttatat ttaacgaaaa taaaaacgta aataagctgg gatttgtagc gcaagacgaa    720
gcgctgcgca caataatacc tacgccaact tttgtaatgg actctggcaa aaatatagat    780
attagcgcag gtataaacct gcagctacag ggggtggagc aagacgcagt tgcgccggca    840
ctggcgtggc tacaagcatt gggcctaaag caaaaccctg cgggcatgcc gtttgttgtg    900
tctgtttcgc gggcgagctt accgtcgcgc tcgccagtgg ggtcctatca attggtggta    960
tcgccaacgc aaattaccat ctttgcccgc gaaccggttg gtgcgtttta cggtatgcaa   1020
tcgttggcga gtgtaatgat agcgggcaga aatactttac ctgtgttaac cgttaacgat   1080
tcgcctcgtt accccttatcg cggtatgcac atagatgtag gtcgtaactt tcattccaaa   1140
caacaaatac tggatgtatt agatcaaatg gcggcgtaca agcttaacaa gctgcatttg   1200
catttgggtg aagatgaagg ctggcgcttg caaatacccca gcttgccaga acttactgat   1260
gtgggcggta agcgctgtca cgatccacaa gaaaacacct gcttattaat gcagcttggg   1320
gcagacgtaa gcggcaaaag tgaacgcgat ggctattaca ctcggcaaga ttatatagag   1380
ctagtaaaag ctgcgaatgc gcgtcacata cagttaatcc cttcttttga tatgcccggt   1440
cattcgcgcg ctgtaataaa agctatggag gcgcgttacc gtaaattcat ggccgctggt   1500
aataaaaaag ccgctgaaca atatttactt tcagacccaa acgataaaac gcagtacaaa   1560
agtattcagt tttattccga taacacgatt aacgcgtgca tggaatctcc ttataaattt   1620
ttaggcaaag taatagacga agtaaaagcc atgcacagcg aagcgggcca gccgcttacg   1680
gtttaccata taggcgcaga tgaaaccgcc ggtgcttggg cgcaatcgcc aatatgccaa   1740
gcgttttttg ccaacaaccc ttacggtgta gaaaatgcca acagctagg tgcttatttt   1800 atcgagcgcg tggccgcatt attagaaact aagggtatta aaaccgcagg ttggagcgat   1860
ggtttaagcc acactaaccc aaaaaatatg cccgccaagg tgcaatcgta tatttgggat   1920
gtattacctt ggggggcgt tgccgaagca aataagcaag ccaatcgagg gtgggatgta   1980
gtgctatctc acccagacgc gctgtatttt gacttcccat acgagccaga cccaaaagaa   2040
ggcggctatt attggggcag ccgccatata gatacccaca aagtatttaa ctatatgccc   2100
ggtaacttac cggctttggc agaggtatac ccaagcccta cccaaacagg gtttgaaata   2160
gcaggcacca ccccattaaa acaaggcgtg caatgggcgg gtatccaagg ccagctgtgg   2220
agcgaaacta tacgcagcga taacgctgtg gaatatatga tctttccgcg tttaattgcc   2280
ttggcagagc gcgcatggca cgcaccaagt tgggagccgc cctacaatta cgagggcgca   2340
acctataatg ctaatagcgg tttattttct gaaaataaaa aaagtgagcg cgataaagcg   2400
```

-continued

```
tggttaaaat tcgcaagcgt cattggctac aaagaattcg ttaagctaga tgccgccgac    2460
attcactacc gcataccaac ggtgggcgct attattcaag actccatgct acacgcaaat    2520
cttgcttacc cagggttagg tattgaatat aaagaagccg gtaaagattg gcagccttac    2580
aacaagccag tacaagtaaa aacgccggta ctggtgcgcg caaaagccgc aacgggggat    2640 agaaagggc gtgcgttacc tgttgagtaa                                     2670
```

<210> SEQ ID NO 8
<211> LENGTH: 1035
<212> TYPE: DNA
<213> ORGANISM: Microbulbifer degradans

<400> SEQUENCE: 8

```
atgttggaga ctaacaatca attgcttggt ccagttattg cggatattgc cggtcaaact      60 cttccgatg aagatatagc gctaataaag aacccgctaa ttggcgggtt aatactgttt     120
acccgtaact attcaacccc ttcacagctt gacgcgctag ttaagcaaat cgcagtgta     180 cgggcagata taattcttgc tgttgaccac gagggtggca gggtgcagcg ctttcgggaa     240
ggctttaccc gcattccagc tatgcaagta tttgccagcg cttataaagc tcgtgccgag     300 ttaaccttg cgcttgcctg taataccggc tggttaatgg ctagtgaact tcgcgcttac     360
gacatagata ttagctttgc accagtattg gatgtggatg atagttttag cagcattat    420 ggcgatagag cttttcttc agaccccaaa gctgttactg cgctagcggg tgcatttata     480
gacggtatgc aacaagcagg tatggcttgt accggtaagc attttcctgg gcatggcagt    540
gtgcgtgccg atagccattt agagctgcca gtggattatc gctcgctcga agctatagag   600
cagctcgatt taatgccttt tgctaagttg caaagtaagc ttgatgctgt aatgcctgcc    660
catatattgt tcccagaggt tgacgatcag cccgttggct tttcttctgt ttggctgcaa    720
aaaatattgc gcgataaaat ggcctacgac ggtgtaattt ttagtgatga tttgacgatg    780
gaaggtgccg ccgtggcggg tagcttcggg gagcgagcca taaaagcaat gagcgctggc    840
tgcgacacat tattggttg caacaatcgc gaggccaccc ttgaggttat tcagacattg     900
gcagataacg gcaactattc tacctctatt cgattgacca gaatgcgggg gaaagcaggg    960
gcgcaaccta tttatgattt acacaataat aaacgctggc aagaaaccaa agaagcatta   1020
ctagcacttg cttaa                                                    1035
```

<210> SEQ ID NO 9
<211> LENGTH: 1632
<212> TYPE: DNA
<213> ORGANISM: Microbulbifer degradans

<400> SEQUENCE: 9

```
atgtttaaaa aaactttagc cgttgcaggg ctagctttag cagcaaacaa tgcattcgca      60
gcaaccaatt gcagtgacct caccgactgg aatagcagca cagcctatac cggtggcacc     120
tcggtaaaac acgccaacag taagtacacc gcccagtggt ggacacaggg tgcagacccg     180
acaagccatt caggccaatg gcaagagtgg aaatttatag atcagtgctc ttcatcgtct     240
agctcaagta gctctagcag cagttccagc tcgtccagca gtagttcaag ctctagcagc     300
tcatcttcaa gctcttccag tagcacctct tcaagttcat ccagctcatc cagttctggc     360
ggcagctgta cagacgcccc cgtctttgca gaaaacaccg catataacac cggcgatgtt     420
gtaaccaact tagaaaattt atacagctgt gttgtacccg gttggtgtaa attgggtggc     480
gcctatgagc caggtcaagg ctgggcgtgg gagcatgctt ggaaccacgt aggtacttgt     540
```

-continued

```
ggtacgtcat cctcttcatc tagctcgtct tccacctcct ctagcagctc aagctcgtct    600
agctcatcca gttcatcaag ctctagcagc tcgtcgtcat ccggcggtgt gggtggcgga    660
aaggtgcctg cacactcact tgtaggctac tggcacaatt ttgttaacgg cgcaggctgc    720
ccaatgcgct taagtgaaat gtcggataag tgggacgtaa ttgacattgc ctttgccgat    780
aacgacccag caagcaatgg taccgtacac tttaatttgt tccccggtac aggcaactgc    840
ccagcaatga atgcagaaca attcaaagcc gatatgcgtg cgctacaggc acaaggtaaa    900
gtatttgtgt tatcgcttgg tggcgcagaa ggcaccataa ccttaaacac cgatgccgac    960
gaagttaatt ttgttaacag cttaactaac ttaattaacg agtggggatt cgatggtgta   1020
gacatagatt tagaaagcgg ctcgcaactt ttgcacggct cgcaaattca gcgcgcctc    1080
attacgtcgc tgcgcaccat tgatgccaat gtaggcggta tggtgttaac catggcacca   1140
gagcatcctt atgtacaagg tggctacatt gcttactcag gaatttgggg tgcgtatttg   1200
ccaattattg atgcgctgcg cgatcagttg gatctactgc atgtgcagct gtataacaat   1260
ggcggcatcc tatcgcctta taccccgcaa acgttccctg caggctcagt agatatgatg   1320
gttgcctctg cacgtatgct tatagaaggc tttaatacgg gcgatggcgg ttacttccaa   1380
ggtttgcgac cagatcaggt atcactaggc ttaccttctg cccaagctc tgctggctct   1440
ggcttggcaa ctaaccaagc aatcatggac gcattggatt gtattacccg aggaacacat   1500
tgcggcacta tcgacgccgg cggcatatac ccgtcattta acggtgtaat gacgtggtcg   1560
ataaactggg atgcccacga tggctatatt ttctctaacc ctattggcga taaggttcac   1620
agcttaccgt aa                                                        1632
```

<210> SEQ ID NO 10
<211> LENGTH: 1271
<212> TYPE: PRT
<213> ORGANISM: Microbulbifer degradans

<400> SEQUENCE: 10

```
Met Asn Leu Thr Lys Phe Ala Val Ala Ala Leu Ser Val Ala Val Leu
  1               5                  10                  15

Ser Ala Cys Gly Gly Gly Ala Gly Asn Ser Pro Ser Pro Gly Ala Gly
                 20                  25                  30

Ser Asn Thr Asn Thr Glu Ser Ala Ser Ser Ser Ser Ser Ser Ser Ser
             35                  40                  45

Ser Ser Ser Thr Ser Ser Thr Ser Ser Ser Ser Ser Ser Ser Ser Gly
         50                  55                  60

Ser Ala Glu Val Asn Val Asp Ile Asp Val Asp Ile Asp Val Glu Asn
 65                  70                  75                  80

Gly Ser Ser Ser Ser Ser Ser Gly Ser Ser Ser Ser Thr Gly
                 85                  90                  95

Gly Gly Asp Ile Thr Ile Ile Asp Glu Ile Glu Ser Ser Thr Ser Ser
                100                 105                 110

Ser Thr Ser Ser Ser Ser Ser Ser Gly Ala Thr Ser Ser Ser Ser Thr
            115                 120                 125

Ser Ser Ser Ser Ser Ser Ser Ser Ser Ser Ser Ser Gly Ala Thr
        130                 135                 140

Gly Ser Ser Ser Ser Ser Ser Gly Ala Gly Ser Thr Ser Ser Ser Ser
145                 150                 155                 160

Ser Ser Ser Ser Ser Ser Ser Ser Ser Ser Ser Ser Ser Ser Ser Ser
                165                 170                 175
```

-continued

```
Ser Ser Ser Ser Ser Ser Thr Gly Gly Asn Ala Gly Val Asp
            180                 185                 190
Ala Glu Leu Gly Tyr Ser Ile Gly Asp Val Tyr Ala Pro Ser Phe Asp
        195                 200                 205
Tyr Thr Ala Val Gly Gly Glu Arg Lys Thr Asp Asn Tyr Arg Val Ile
210                 215                 220
Gly Tyr Tyr Met Pro Ser Leu Asp Gly Ser Phe Pro Pro Ser Ala Ile
225                 230                 235                 240
Gly Glu Gln Gln Ala Gln Met Leu Thr His Ile Asn Tyr Ala Phe Ile
            245                 250                 255
Gly Ile Asn Ser Gln Leu Glu Cys Asp Phe Ile Asp Val Glu Lys Ala
            260                 265                 270
Asp Ala Glu Thr Gln Ile Ile Ala Glu Leu Gln Ala Leu Lys Asn Trp
            275                 280                 285
Asn Ala Asp Leu Lys Ile Leu Phe Ser Val Gly Gly Trp Ala Glu Ser
            290                 295                 300
Asn Asp Ala Ala Glu Thr Val Ser Arg Tyr Arg Asp Ala Phe Ala Pro
305                 310                 315                 320
Ala Asn Arg Glu His Phe Val Ser Ser Cys Val Ala Phe Met Gln Gln
                325                 330                 335
His Gly Phe Asp Gly Ile Asp Ile Asp Trp Glu Tyr Pro Arg Ala Glu
            340                 345                 350
Asp Val Asp Asn Phe Ile Ala Gly Leu Ala Ala Met Arg Asn Gln Leu
            355                 360                 365
Asp Ala Arg Gly Asn Gly Glu Leu Val Thr Ile Ala Gly Ala Gly Gly
            370                 375                 380
Ala Phe Phe Leu Ser Arg Tyr Tyr Ser Lys Leu Ala Ala Ile Val Glu
385                 390                 395                 400
Gln Leu Asp Phe Ile Asn Leu Met Thr Tyr Asp Leu Asn Gly Pro Trp
            405                 410                 415
Asn Gly Val Thr Lys Thr Asn Phe His Ala His Leu Tyr Gly Asn Asn
            420                 425                 430
Gln Glu Pro Arg Phe Tyr Asn Ala Leu Arg Glu Ala Asp Leu Gly Leu
            435                 440                 445
Thr Trp Glu Glu Ile Val Glu Arg Phe Pro Ser Pro Phe Glu Leu Thr
            450                 455                 460
Val Asp Ala Ala Ile Lys Gln His Leu Met Met Asp Ile Pro Arg Glu
465                 470                 475                 480
Lys Ile Val Met Gly Val Pro Phe Tyr Gly Arg Ala Phe Phe Asn Thr
                485                 490                 495
Gly Ser Ser Asn Thr Gly Leu Tyr Gln Thr Phe Asn Thr Pro Asn Gly
            500                 505                 510
Asp Pro Tyr Val Gly Asp Ala Ser Leu Leu Val Gly Cys Glu Ala Cys
            515                 520                 525
Glu Ala Arg Gly Glu Pro Arg Ile Ala Thr Phe Asn Asp Ile Gln Gln
            530                 535                 540
Leu Ile Glu Gly Asn Tyr Gly Tyr Thr Arg His Phe Asp Asp Gln Thr
545                 550                 555                 560
Lys Ala Pro Trp Leu Tyr His Ala Glu Asn Asn Ile Phe Val Thr Tyr
            565                 570                 575
Asp Asp Ala Gln Ser Leu Val Tyr Lys Thr Asp Tyr Ile Lys Gln Gln
            580                 585                 590
```

-continued

```
Gly Leu Gly Gly Ala Met Phe Trp His Leu Gly Gln Asp Asp Ser Gln
            595                 600                 605
Phe Thr Leu Leu Ala Thr Leu His Thr Glu Leu Asn Gly Ala Asn Ala
        610                 615                 620
Gly Ser Leu Gln Gly Gly Asn Ser Glu Thr Asp Asn Thr Thr Asp Glu
625                 630                 635                 640
Thr Glu Gly Asn Asn Glu Asp Asn Thr Glu Gln Asn Pro Glu Glu Asn
                645                 650                 655
Thr Asp Thr Glu Glu Thr Glu Thr Glu Thr Glu Thr Glu Thr Glu Thr
            660                 665                 670
Glu Thr Glu Thr Glu Thr Ser Val Glu Gln Pro Thr Ala Pro
        675                 680                 685
Thr Ile Ala Trp Met Asn Thr Ser Tyr Thr Gly Ser Ser Val Thr Val
        690                 695                 700
Thr Ile Thr Trp Asn Met Tyr Trp Gly Thr Asn Gly Asn Gln Trp Gln
705                 710                 715                 720
Leu Trp Leu Asp Gly Glu Gln Val Tyr Ser Ala Asn Leu Thr Thr Asn
                725                 730                 735
Gly Gln Asn Ala Gln Thr Asp Ser Lys Ile Thr Ile Thr Gly Ala
            740                 745                 750
Gly Ala His Ser Val Glu Val Lys Leu Cys Asn Gln Gln Asp Ile Asn
        755                 760                 765
Val Ser Cys Ala Ser Asp Ser Glu Thr Ile Thr Leu Gln Gly Gly Ser
        770                 775                 780
Asp Gly Ala Thr Ser Ser Ser Ser Ser Thr Ser Ser Ser Ser Ser
785                 790                 795                 800
Ser Ser Ser Ser Ser Thr Gly Gly Ser Thr Ser Ser Thr Ser Ser Ser
                805                 810                 815
Ser Ser Ser Thr Ser Ser Ser Ser Ser Ser Ser Ser Ser Ser Ser
            820                 825                 830
Ser Thr Ser Gly Gly Gly Glu Thr Asp Leu Ser Gly Val Val Tyr Gly
        835                 840                 845
Glu Tyr Asn Asn Thr Tyr Lys Gln Thr Ser Asp Lys Ile Ile Val Thr
        850                 855                 860
Tyr Phe Val Glu Trp Gly Ile Tyr Gly Arg Asp Tyr His Val Asn Asn
865                 870                 875                 880
Ile Pro Ala Ser Asn Leu Thr His Val Leu Phe Gly Phe Ile Ala Met
                885                 890                 895
Cys Gly Asp Asn Pro His Ala Ser Gly Gly Ala Gln Ala Ala Ile Ala
            900                 905                 910
Ser Glu Cys Ala Asp Lys Gln Asp Phe Glu Val Thr Leu Val Asp Arg
        915                 920                 925
Phe Ala Asn Leu Glu Lys Thr Tyr Pro Gly Asp Thr Trp Tyr Asp Asp
        930                 935                 940
Thr Thr Gly Gln Asp Tyr Asn Gly Asn Phe Gly Gln Leu Arg Lys Leu
945                 950                 955                 960
Lys Ala Gln His Pro His Leu Lys Ile Leu Pro Ser Ile Gly Gly Trp
                965                 970                 975
Thr Met Ser Thr Pro Phe Tyr Glu Met Ala Lys Asn Glu Ala Asn Arg
            980                 985                 990
Ala Val Phe Val Glu Ser Ala Val Asn Phe Ile Lys Lys Tyr Asp Phe
        995                 1000                1005
Phe Asp Gly Val Asp Ile Asp Trp Glu Tyr Pro Val Tyr Gly Gly Thr
```

-continued

```
                1010                1015                1020
Ala Pro Glu Leu Ser Thr Ala Ala Asp Arg Asp Ala Tyr Thr Ala Leu
1025                1030                1035                1040

Met Arg Asp Leu Arg Ala Ala Leu Asp Glu Leu Ala Glu Glu Thr Gly
                1045                1050                1055

Arg Glu Tyr Glu Ile Thr Ser Ala Val Gly Ala Ala Pro Glu Lys Ile
            1060                1065                1070

Ala Ala Val Asp Tyr Ala Ser Ala Thr Thr Tyr Met Asp Tyr Ile Phe
        1075                1080                1085

Leu Met Ser Tyr Asp Tyr Met Gly Ala Trp Ala Asn Thr Thr Gly His
    1090                1095                1100

His Thr Pro Leu Tyr Asn Asn Asn Glu Glu Arg Glu Gly Phe Asn Thr
1105                1110                1115                1120

His Ala Ser Val Gln Asn Leu Leu Thr Ala Gly Val Pro Ser Ser Lys
                1125                1130                1135

Leu Val Val Gly Gly Ala Phe Tyr Gly Arg Gly Trp Val Gly Thr Gln
            1140                1145                1150

Asn Thr Asn Ala Ala Lys Ser Asp Leu Phe Pro Leu Tyr Gly Gln Ala
        1155                1160                1165

Ser Gly Ala Ala Lys Gly Thr Trp Glu Ala Gly Val Gln Asp Tyr Arg
    1170                1175                1180

Asp Leu Tyr Asp Asn Tyr Ile Gly Thr Asn Gly Thr Gly Ile Asn Gly
1185                1190                1195                1200

Phe Ser Ala His Tyr Asp Glu Ile Ala Glu Ala Ala Tyr Leu Trp Asn
                1205                1210                1215

Ser Ser Thr Gly Glu Phe Ile Ser Tyr Asp Ser Pro Arg Ser Ile Ala
            1220                1225                1230

Ala Lys Ala Asp Tyr Val Lys Gln Tyr Asn Leu Ala Gly Met Leu Thr
        1235                1240                1245

Trp Glu Ile Asp Gly Asp Asn Gly Gln Leu Leu Asn Ala Ile Asn Glu
    1250                1255                1260

Ser Phe Gly Asn Glu Lys Gln
1265                1270

<210> SEQ ID NO 11
<211> LENGTH: 792
<212> TYPE: PRT
<213> ORGANISM: Microbulbifer degradans

<400> SEQUENCE: 11

Met Asn Pro Ile Ala Lys Leu Thr Leu Ala Thr Gly Ala Met Leu Ser
1               5                   10                  15

Ala His Val Ala Tyr Ala Tyr Asp Cys Asp Gly Leu Ala Thr Trp Asn
            20                  25                  30

Ala Ser Ser Ala Tyr Ala Gly Ser Thr Val Val Gln His Ser Asn Val
        35                  40                  45

Ala Tyr Lys Ala Asn Trp Trp Thr Gln Asn Gln Asn Pro Ala Ser His
    50                  55                  60

Ser Gly Pro Trp Gln Glu Trp Thr Asn Leu Gly Asn Cys Asp Gly Asp
65                  70                  75                  80

Gly Gly Gly Asn Thr Asn Gln Ala Pro Ser Ala Asn Ala Asn Gly Pro
                85                  90                  95

Tyr Ala Ala Gln Leu Gly Ala Ala Ile Ala Phe Ser Ser Ala Gly Ser
            100                 105                 110
```

```
Ser Asp Ser Asp Gly Asn Ile Ala Ser Tyr Asn Trp Thr Phe Gly Asp
        115                 120                 125

Gly Asn Ser Ser Asn Gln Ala Ser Pro Ser His Thr Tyr Gly Ser Gln
        130                 135                 140

Gly Thr Tyr Ala Val Thr Leu Thr Val Thr Asp Asn Glu Gly Ala Ser
145                     150                 155                 160

Ser Ser Ala Thr Thr Ser Ala Ser Val Thr Gln Gly Gly Asp Pro Gly
                165                 170                 175

Asp Cys Gln Ala Pro Gln Tyr Ser Ala Gly Thr Gln Tyr Ala Ala Gly
            180                 185                 190

Asp Ile Val Ala Asn Gly Gly Asn Leu Tyr Gln Cys Asn Ile Ala Gly
            195                 200                 205

Trp Cys Ser Ser Ala Ala Trp Ala Tyr Ala Pro Gly Thr Gly Ala
210                     215                 220

His Trp Gln Asp Ala Trp Ser Leu Thr Ser Glu Cys Asp Asp Asn Gly
225                 230                 235                 240

Asn Thr Asn Gln Ala Pro Thr Ala Asn Ala Asn Gly Pro Tyr Ser Gly
                245                 250                 255

Ser Ala Gly Ile Ser Ile Ser Phe Ser Ser Asn Gly Ser Ala Asp Ser
            260                 265                 270

Asp Gly Thr Ile Ala Ser Tyr Ser Trp Asn Phe Gly Asp Gly Ala Ser
        275                 280                 285

Ser Ser Gln Ala Asn Pro Ser His Ser Tyr Met Asn Glu Gly Thr Tyr
        290                 295                 300

Gln Val Ser Leu Thr Val Thr Asp Asp Gly Ala Ser Ala Thr Ala
305                 310                 315                 320

Phe Thr Thr Ala Asn Val Thr Gly Asn Gly Glu Asn Gln Glu Pro Val
                325                 330                 335

Ala Ser Ile Ser Ala Pro Ser Ala Ser Glu Gly Ala Ser Val Asn
                340                 345                 350

Phe Ser Ser Ala Gly Ser Asn Asp Pro Asp Gly Ser Ile Val Ser Tyr
        355                 360                 365

Ser Trp Asn Phe Gly Asp Gly Thr Ser Ser Gln Gln Ala Asn Pro Ser
370                 375                 380

His Thr Tyr Ser Ser Ala Gly Ser Tyr Ser Val Ser Leu Thr Val Val
385                 390                 395                 400

Asp Asn Glu Gly Ala Asn Asn Val Ala Asn His Ser Ile Thr Ile Ser
                405                 410                 415

Gly Asp Thr Gly Gly Thr His Gly Asp Lys Ile Ile Gly Tyr Phe
            420                 425                 430

Ala Glu Trp Gly Val Tyr Gly Arg Asn Tyr His Val Lys Asn Ile His
        435                 440                 445

Thr Ser Gly Ser Ala Asp Lys Leu Thr His Ile Val Tyr Ala Phe Gly
        450                 455                 460

Asn Val Gln Asn Gly Glu Cys Lys Ile Gly Asp Ser Tyr Ala Ala Tyr
465                 470                 475                 480

Asp Lys Ala Tyr Ser Ala Asp Ser Val Asp Gly Val Ala Asp Thr
                485                 490                 495

Trp Asp Asp Gly Val Leu Arg Gly Asn Phe Gly Gln Leu Arg Arg Leu
            500                 505                 510

Lys Ala Met His Pro Gln Ile Lys Ile Val Trp Ser Phe Gly Gly Trp
            515                 520                 525

Thr Trp Ser Gly Gly Phe Gly Glu Ala Ala Ala Asn Ala Asp His Phe
```

```
                530                 535                 540
Ala Asn Ser Cys Tyr Asp Leu Val Phe Asp Ala Arg Trp Ala Asp Val
545                 550                 555                 560

Phe Asp Gly Ile Asp Ile Asp Trp Glu Tyr Pro Asn Asp Cys Gly Leu
                565                 570                 575

Ser Cys Asp Asn Ser Gly Tyr Asp Gly Tyr Arg Val Leu Met Gln Ala
                580                 585                 590

Leu Arg Asn Arg Phe Gly Asn Lys Leu Val Thr Ala Ala Ile Gly Ala
                595                 600                 605

Gly Glu Ser Lys Gln Asn Ala Ala Asp Tyr Gly Gly Ala Ala Gln Tyr
                610                 615                 620

Leu Asp Phe Tyr Met Leu Met Thr Tyr Asp Phe Phe Gly Ala Phe Asn
625                 630                 635                 640

Pro Gln Gly Pro Thr Ala Pro His Ser Pro Leu Tyr Asn Tyr Pro Gly
                645                 650                 655

Met Pro Ile Glu Gly Phe Ser Ser Asp His Gly Ile Gln Val Leu Lys
                660                 665                 670

Ser Lys Gly Val Pro Ala Glu Lys Ile Leu Leu Gly Ile Gly Phe Tyr
                675                 680                 685

Gly Arg Gly Trp Thr Asn Val Thr Gln Asp Ala Pro Gly Gly Ser Ala
                690                 695                 700

Asn Gly Ala Ala Pro Gly Thr Tyr Glu Lys Gly Ile Glu Asp Tyr Lys
705                 710                 715                 720

Val Leu Lys Asn Thr Cys Pro Ala Thr Gly Thr Ile Ala Gly Thr Ala
                725                 730                 735

Tyr Ala Lys Cys Gly Ser Asn Trp Trp Gly Tyr Asp Thr Pro Ala Thr
                740                 745                 750

Ile Asp Ser Lys Met Asp Tyr Ala Lys Gln Gln Gly Leu Gly Gly Ala
                755                 760                 765

Phe Phe Trp Glu Leu Ser Gly Asp Thr Thr Asp Gly Glu Leu Ile Arg
770                 775                 780

Ala Ile Asp Asn Gly Leu Lys Asn
785                 790

<210> SEQ ID NO 12
<211> LENGTH: 448
<212> TYPE: PRT
<213> ORGANISM: Microbulbifer degradans

<400> SEQUENCE: 12

Met Gln Pro Ile Lys Ser Thr Lys Arg Asn Leu Ile Met Phe Ala Lys
1               5                   10                  15

Lys Ile Thr Tyr Ser Thr Ile Ala Leu Ala Ile Ala Gly Leu Ser Gly
                20                  25                  30

Asn Ala Leu Ser His Gly Leu Met Val Asp Pro Ser Arg Asn Ala
            35                  40                  45

Leu Cys Gly Met Ile Glu Lys Pro Asp Gln Ala Thr Ser Pro Ala Cys
        50                  55                  60

Gln Gln Ala Phe Gln Asn Asp Phe Asn Gly Tyr Gln Phe Met Ser
65                  70                  75                  80

Val Leu Thr His Asp Ile Gly Arg Gln Gly Thr Ser Asn Asn Val
                85                  90                  95

Cys Gly Phe Asp Ser Glu Thr Trp Asn Gly Gly Ala Thr Pro Trp Asp
                100                 105                 110
```

```
Ala Ala Ile Asp Trp Pro Thr Thr Gln Ile Ser Ser Gly Pro Leu Glu
        115                 120                 125

Ile Asp Trp Asn Ile Ser Trp Gly Pro His Trp Asp Asp Thr Glu Glu
    130                 135                 140

Phe Val Tyr Tyr Ile Thr Lys Pro Asp Phe Val Tyr Gln Val Gly Val
145                 150                 155                 160

Pro Leu Ser Trp Ser Asp Phe Glu Ala Thr Pro Phe Cys Gln Leu Asp
                165                 170                 175

Tyr Ser Asp Ala Asn Pro Asn Ala Asn Pro Gly Val Ser Thr Thr Lys
            180                 185                 190

Ser Ala Asn Leu Phe His Thr Gln Cys Asn Val Pro Ala Arg Ser Gly
        195                 200                 205

Arg His Val Ile Tyr Gly Glu Trp Gly Arg Asn Tyr Phe Thr Tyr Glu
210                 215                 220

Arg Phe His Gly Cys Met Asp Val Thr Phe Gly Gly Ser Asn Pro Pro
225                 230                 235                 240

Pro Ser Asn Gln Ala Pro Thr Ala Asn Ala Gln Ser Val Asn Val Ser
                245                 250                 255

Ser Gly Ser Ser Val Ser Ile Thr Leu Ser Gly Ser Asp Val Asp Gly
            260                 265                 270

Val Ile Ser Ser Tyr Ala Ile Ala Ala Pro Ser Asn Gly Ser Leu
        275                 280                 285

Ser Gly Ser Gly Ala Gln Arg Leu Tyr Thr Pro Asn Gly Asn Phe Ser
    290                 295                 300

Gly Ser Asp Ser Phe Gln Phe Thr Val Thr Asp Asp Gly Ala Thr
305                 310                 315                 320

Ser Asn Ala Ala Thr Val Ser Ile Asn Val Ser Ser Gln Pro Glu Pro
                325                 330                 335

Glu Pro Glu Pro Glu Pro Glu Pro Glu Pro Gly Thr Gly Ala
            340                 345                 350

Ser Cys Glu His Val Val Val Asn Ala Trp Asp Ser Gly Phe Gln Gly
        355                 360                 365

Ala Ile Arg Ile Thr Asn Thr Ser Asp Gln Asn Ile Asn Gly Trp Asn
    370                 375                 380

Val Ser Trp Ser Tyr Asn Asn Gly Thr Thr Ile Ser Gln Leu Trp Asn
385                 390                 395                 400

Ala Asn Phe Ser Gly Ser Asn Pro Tyr Ser Ala Ser Asn Leu Gly Trp
                405                 410                 415

Asn Ala Thr Ile Gln Pro Gly Gln Thr Val Glu Phe Gly Phe Thr Gly
            420                 425                 430

Asn Gly Ser Val Pro Ala Ala Pro Ala Val Thr Gly Ala Val Cys Asn
        435                 440                 445

<210> SEQ ID NO 13
<211> LENGTH: 1146
<212> TYPE: PRT
<213> ORGANISM: Microbulbifer degradans

<400> SEQUENCE: 13

Met Lys Asn Lys His Cys Leu Ala Ala Leu Ala Leu Ala Ile Ser Thr
1               5                   10                  15

His Ala Tyr Ala Ala Pro Gly Thr Pro Asn Ile Ala Trp Leu Pro Ala
            20                  25                  30

Thr His Glu Ser Gly Glu Ala Ile Asn Val His Trp Asp Met Trp Trp
        35                  40                  45
```

-continued

```
Gly Glu Asn Gly Thr Glu Trp Gln Leu Thr Asp Asn Gly Asp Leu Arg
 50                  55                  60
Cys Ser Gly Ser Leu Thr Ala Asn Gly Gln Asn Gln Gln Ser Ala Glu
 65                  70                  75                  80
Cys Ala Ala Asn Tyr Ser Ser Gly Ser His Ala Leu Gln Val Ser Leu
                 85                  90                  95
Cys Asn Thr Ser Gly Cys Ser Glu Ser Asn Val Val Thr Ile Asn Val
             100                 105                 110
Asn Gln Gly Ala Ser Ser Asn Val Pro Pro Gln Val Ser Ile Ser Ala
         115                 120                 125
Pro Ala Ser Ala Gly Glu Gly Asp Ser Ile Thr Leu Ser Ala Thr Ala
 130                 135                 140
Ser Asp Ser Asp Gly Thr Ile Thr Ser Val Thr Phe Leu Val Asp Gly
 145                 150                 155                 160
Ile Ala Ile Ala Thr Asp Thr Thr Ser Pro Tyr Ser Thr Asn Trp Ile
                 165                 170                 175
Ala Lys Ala Gly Thr His Ser Leu Thr Ala Gln Ala Leu Asp Asn Gln
             180                 185                 190
Asn Ala Thr Gly Asp Asp Ser Val Ser Ile Ser Val Thr Ser Ala Pro
         195                 200                 205
Asn Gln Leu Pro Ser Val Ser Leu Val Ala Pro Asn Ala Asn Leu Met
 210                 215                 220
Ala Gly Ser Glu Thr Ser Phe Glu Ile Asn Ala Ser Asp Ala Gly Gly
 225                 230                 235                 240
Ser Ile Ser Ser Val Glu Leu Tyr Leu Asn Gly Asn Leu Leu Gly Thr
                 245                 250                 255
Asp Thr Ser Ala Pro Tyr Asn Val Ser Trp Thr Ala Glu Ala Gly Asp
             260                 265                 270
His Ser Ile Tyr Ala Val Ala Ser Asp Asp Arg Gly Gly Val Ser Gln
         275                 280                 285
Ser Asp Thr Val Phe Leu Thr Val Ala Glu Asp Thr Asn Ala Ala Pro
 290                 295                 300
Ser Val Ser Leu Ser Thr Val Pro Thr Asp Ala Met Glu Gly Asp Ala
 305                 310                 315                 320
Leu Thr Leu Glu Ala Ala Ala Ser Asp Ser Asp Gly Ser Val Ala Gln
                 325                 330                 335
Val Asp Phe Tyr Leu Asn Asn Gln Leu Leu Gly Ser Ala Thr Ser Ala
             340                 345                 350
Pro Tyr Ser Leu Gln Trp Thr Ala Thr Arg Gly Ser His Thr Leu Arg
         355                 360                 365
Ala Thr Ala Val Asp Asn Gln Gly Lys Thr Ala Ser Ala Ile Ser Thr
 370                 375                 380
Phe Ser Val Ala Ala Asp Thr Ser Ala Ser His Glu Asp Cys Arg Pro
 385                 390                 395                 400
Asp Gly Leu Tyr Ala Thr Pro Glu Val Gln Ser Pro Tyr Cys Thr Val
                 405                 410                 415
Tyr Asp Ile Gln Gly Arg Glu Leu Met Gly Ser Ala Thr Arg Arg Val
             420                 425                 430
Ile Gly Tyr Phe Thr Ser Trp Arg Thr Gly Gly Asn Gly Pro Ala Tyr
         435                 440                 445
Leu Ala His Gln Ile Pro Trp Asp Lys Leu Thr His Ile Asn Tyr Ala
 450                 455                 460
```

-continued

```
Phe Ala His Val Asp Gly Asn His Val Ser Ile Gly Ala Asn Thr
465                 470                 475                 480

Pro Thr Asn Ala Ala Thr Gly Met Glu Trp Pro Asp Val Ala Gly Ala
                485                 490                 495

Glu Met Asp Pro Ser Phe Ser Tyr Lys Gly His Phe Asn Leu Leu Asn
                500                 505                 510

Lys Tyr Lys Lys Gln Tyr Pro His Val Lys Thr Leu Ile Ser Ile Gly
            515                 520                 525

Gly Trp Ala Glu Thr Gly Gly Tyr Phe Asp Ser Asn Gly Asp Arg Val
        530                 535                 540

Asn Ser Gly Gly Phe Tyr Thr Met Thr Thr Asn Ala Asp Gly Ser Val
545                 550                 555                 560

Asn Thr Ala Gly Ile Asn Thr Phe Ala Asp Ser Val Val Glu Phe Leu
                565                 570                 575

Arg Thr Tyr Ser Phe Asp Gly Ala Asp Ile Asp Tyr Glu Tyr Pro Thr
                580                 585                 590

Ser Met Asn Asp Ala Gly Asn Pro Ser Asp Phe Ala Ile Ala Asn Ala
            595                 600                 605

Arg Arg Lys Gly Leu Asn Ala Ser Tyr Asn Val Leu Met Lys Thr Leu
610                 615                 620

Arg Gln Lys Leu Asp Ile Ala Gly Glu Gln Asp Gly Lys His Tyr Met
625                 630                 635                 640

Leu Thr Ile Ala Ser Pro Ser Ser Gly Tyr Leu Leu Arg Gly Met Glu
                645                 650                 655

Ala Phe Glu Ala Thr Gln Tyr Leu Asp Tyr Val Asn Ile Met Ser Tyr
                660                 665                 670

Asp Leu His Gly Ala Trp Asn Gln Phe Val Gly Pro Asn Ala Ala Leu
            675                 680                 685

Phe Asp Asn Gly Gln Asp Ala Glu Leu Ile Gln Trp Asn Ala Tyr Gly
690                 695                 700

Gly Gln Tyr Lys Asn Ile Gly Tyr Leu Asn Thr Asp Trp Ala Tyr His
705                 710                 715                 720

Tyr Phe Arg Gly Ala Met Pro Ala Gly Arg Ile Asn Ile Gly Val Pro
                725                 730                 735

Tyr Tyr Thr Arg Gly Trp Gln Gly Val Thr Gly Gly Thr Asn Gly Leu
            740                 745                 750

Trp Gly Gln Ala Ser Leu Pro Asn Gln Ser Glu Cys Pro Val Gly Thr
        755                 760                 765

Gly Gly Ser Ala Thr Ser Lys Cys Gly Asn Gly Ala Val Gly Ile Asp
        770                 775                 780

Asn Leu Trp His Asp Lys Asp Glu Asn Gly Asn Glu Met Gly Ala Gly
785                 790                 795                 800

Ser Asn Pro Met Trp His Ala Lys Asn Leu Glu Asn Asn Ile Leu Gly
                805                 810                 815

Asp Tyr Leu Thr Ala Tyr Gly Leu Asp Pro Ile Asn Asn Pro Asp His
                820                 825                 830

Gln Leu Ser Gly Asn Tyr Gln Arg Tyr Tyr Asp Asp Val Leu Val Ala
            835                 840                 845

Pro Trp Leu Trp Asn Ala Ala Lys Gln Val Phe Ile Ser Thr Glu Asp
850                 855                 860

Glu Gln Ser Ile Asn Arg Lys Ala Asp Tyr Val Val Glu Asn Gly Ile
865                 870                 875                 880

Gly Gly Ile Met Phe Trp Glu Leu Ala Gly Asp Tyr Gln Phe Asn Ala
```

-continued

```
                885                 890                 895
Ala Lys Gly Gln Tyr Glu Met Gly His Thr Leu Thr Thr Ala Ile Ala
            900                 905                 910

Asp Lys Phe Ala Asn Ala Pro Ala Tyr Gly Asn Gln Arg Ala Glu Ile
        915                 920                 925

Asp Met Pro Gln Gln Thr Leu Asp Ile Gly Ile Lys Leu Thr Asn Phe
    930                 935                 940

Ala Leu Gly Asp Asn Asn Phe Pro Ile Thr Pro Asp Leu Ile Ile Thr
945                 950                 955                 960

Asn Asn Thr Gly Gln Asn Leu Pro Gly Gly Thr Glu Phe Tyr Phe Asp
                965                 970                 975

Ile Ala Thr Ser Thr Pro Asp Asn Met Gly Asp Gln Ser Ala Ala Ser
            980                 985                 990

Leu Thr Ile Val Ser Asn Gly Ser Asn Ala Ala Gly Asn Asn Val Gly
        995                 1000                1005

Gly Leu Glu Asn Asn Phe His Arg Val Lys Ile Ser Thr Pro Ser Tyr
    1010                1015                1020

Leu Thr Leu Ala Asp Gly Glu Glu Trp Lys Val Val Leu Lys Tyr Tyr
1025                1030                1035                1040

Leu Pro Val Ser Met Pro Ser Asn Trp Val Val Asn Val Ala Gly Glu
                1045                1050                1055

Glu Phe Ala Leu Ser Ser Glu Tyr Pro Asn Leu Pro Met Gly Ser Ile
            1060                1065                1070

Ser Ser Gly Gly Gly Asn Asn Gly Gly Asn Thr Gly Gly Asp Cys
        1075                1080                1085

Ser Asn Ala Ser Asp Tyr Pro Ala Tyr Pro Asn Phe Pro Gln Lys Asp
    1090                1095                1100

Trp Ala Gly Asn Pro Ser His Ala Asn Ala Gly Asp Arg Met Thr His
1105                1110                1115                1120

Asn Asn Ala Leu Tyr Glu Ala Lys Trp Trp Thr Ser Ala Thr Pro Gly
                1125                1130                1135

Thr Ser Asp Trp Asp Leu Val Cys Thr Phe
            1140                1145

<210> SEQ ID NO 14
<211> LENGTH: 795
<212> TYPE: PRT
<213> ORGANISM: Microbulbifer degradans

<400> SEQUENCE: 14

Met Lys Leu Arg Leu Leu Pro His Ser Ile Ser Leu Ala Ser Leu Leu
 1               5                  10                  15

Leu Leu Ser Ala Cys Gln Gln Glu His Ala Thr Ser Thr Asn Ala Gln
            20                  25                  30

Leu Ser Pro Ile Ala Pro Pro Ala Ile Ser Ile Val Pro Ala Pro Val
        35                  40                  45

Ser Ala Glu Ile Lys Thr Gly Gln Phe Val Phe Gly Asn Ser Thr Gln
    50                  55                  60

Leu Thr Val Asn Ser Glu Lys Leu Arg Asp Val Ala Gln Leu Trp Ala
65                  70                  75                  80

Asp Phe Phe Asn Val Ala Ser Gly Ile Asn Leu Gln Val Gln Ser Ala
                85                  90                  95

Thr Gly Asn Ser Asp Glu Ala Asn Ser Val Ser Leu Glu Leu Val Pro
            100                 105                 110
```

-continued

```
Ala Ser Glu Phe Ser Ser Ser Asn Ala Glu Ala Tyr Glu Leu Thr Val
        115                 120                 125
Thr Asp Asn Ala Ile Thr Val Arg Ala Ser Thr Arg Ala Gly Ile Phe
130                 135                 140
Tyr Gly Leu Thr Ser Leu Arg Gln Leu Leu Pro Pro Gln Ile Glu Ser
145                 150                 155                 160
Pro Ser Pro Ile Asn Ser Val Asn Trp Val Pro Ala Val Ala Ile
                165                 170                 175
Val Asp Glu Pro Leu Tyr Pro Tyr Arg Gly Met His Leu Asp Val Ser
            180                 185                 190
Arg His Phe Phe Asp Val Asn Phe Ile Lys Arg Tyr Ile Asp Ile Leu
        195                 200                 205
Ala Phe His Lys Met Asn Arg Phe His Trp His Leu Thr Asp Asp Gln
210                 215                 220
Gly Trp Arg Ile Pro Ile Asp Ala Tyr Pro Leu Leu Thr Glu Lys Ser
225                 230                 235                 240
Ala Trp Arg Asp Lys Thr Val Ile Gly His Thr Tyr Asp Arg Asp Val
                245                 250                 255
Ala Tyr Asn Thr Asn Arg Ile Gly Gly Phe Tyr Ser Lys Glu Gln Ile
            260                 265                 270
Arg Asp Ile Val Ala Tyr Ala Ala Glu Arg Gln Ile Met Val Ile Pro
        275                 280                 285
Glu Ile Asp Val Pro Gly His Ala Ala Ala Ile Leu His Ala Tyr Pro
290                 295                 300
Glu Phe Gly Cys Ile Glu Gln Val Ser Gln Val Gln Ser Asn Phe Gly
305                 310                 315                 320
Ile Phe Glu Gln Val Leu Cys Pro Thr Glu Pro Thr Phe Glu Phe Leu
                325                 330                 335
Arg Ala Val Phe Thr Glu Val Ala Glu Leu Phe Pro Gly Glu Tyr Leu
            340                 345                 350
His Val Gly Gly Asp Glu Val Lys Lys Val Gln Trp Gln Gln Ser Pro
        355                 360                 365
Phe Val Thr Glu Leu Met Gln Arg Glu Gly Leu Lys Asp Tyr His Glu
370                 375                 380
Val Gln Ser Tyr Phe Ile Cys Arg Val Gly Glu Ile Val Ser Ser Leu
385                 390                 395                 400
Asp Lys Lys Met Leu Gly Trp Asn Glu Ile Leu Asp Gly Gly Ile Ala
                405                 410                 415
Pro Asn Ala Thr Ile Met Ser Trp Gln Gly Val Glu Gly Gly Ile Ala
            420                 425                 430
Ala Ala Glu Leu Gly His Asp Ala Ile Met Ser Pro Gly Asn Tyr Val
        435                 440                 445
Tyr Phe Asp His Phe Gln Ser Arg Ser Val Asp Glu Pro Leu Ala Ile
450                 455                 460
His Gly Ile Thr Pro Leu Ser Glu Thr Tyr Ser Tyr Asn Pro Met Pro
465                 470                 475                 480
Glu Gln Phe Ala Gly Thr Glu Lys Ala Lys His Ile Leu Gly Ala Gln
                485                 490                 495
Gly Gln Leu Trp Thr Glu Tyr Val Pro Thr Thr Ala Lys Ala Glu Tyr
            500                 505                 510
Met Ile Leu Pro Arg Leu Ser Ala Val Ala Glu Ile Thr Trp Thr Pro
        515                 520                 525
Val Asn Lys Gln Ser Trp Gln Ser Phe Ser Glu Arg Leu Pro Ser Leu
```

```
                530                 535                 540
Phe Ala Arg Phe Asp Glu Met Gly Leu Asn Ala Ala Arg Ser Val Tyr
545                 550                 555                 560

Ala Ile Thr Ala Thr Ala Lys Thr Glu Gly Ser Gly Glu Asp Ala Lys
                565                 570                 575

Tyr Arg Val Asn Leu Ala Ser Asp Thr Ala His Val Ile Ile Arg Tyr
                580                 585                 590

Thr Thr Asp Gly Thr Leu Pro Asn Ala Gln Ser Pro Ile Tyr Ser Glu
                595                 600                 605

Pro Phe Leu Val Glu Gly Asp Thr Phe Val Arg Ala Arg Ser Gln Asp
610                 615                 620

Lys Ile Ser Gly Asn Phe Tyr Leu Glu Ser Gln Leu Arg Thr Val Lys
625                 630                 635                 640

His Lys Ala Val Gly Ala Lys Leu Thr Leu Leu Ser Glu Ala Asn Thr
                645                 650                 655

Glu Trp Asn Lys Asp Pro Val Lys Thr Leu Ser Asp Gly Ile Thr Ser
                660                 665                 670

Ile Asp Gln Ile Phe Gln Leu Asp Asp Trp Ala Thr Phe Phe Gly Asp
                675                 680                 685

Glu Val Val Ala His Ile Thr Phe Ala Lys Ala Gln Thr Val Ser Glu
                690                 695                 700

Val Ser Ile Gly Phe Asn Pro Gly Lys His Arg Gln Met Tyr Pro Pro
705                 710                 715                 720

Thr Arg Leu His Ile Leu Ser Ser Ser Asp Gly Glu Thr Trp Gln Ser
                725                 730                 735

Leu Gly Glu Ala Asp Pro Gln His Leu Ala Thr Ala Lys Asn Arg Val
                740                 745                 750

Ser Tyr Thr Phe Ala Pro Thr Thr Arg His Leu Arg Ile Glu Ala
                755                 760                 765

Glu Asn Lys Thr Arg Val Leu Ser Thr Glu Ser Gly Lys Leu Lys Ser
770                 775                 780

Val Pro Leu Tyr Leu Asp Glu Ile Ile Val Lys
785                 790                 795

<210> SEQ ID NO 15
<211> LENGTH: 889
<212> TYPE: PRT
<213> ORGANISM: Microbulbifer degradans

<400> SEQUENCE: 15

Met Ala Leu Phe Ser Lys Tyr Val Trp Gln Val Ala Val Ala Gly Ala
1               5                   10                  15

Leu Gly Thr Val Ser Leu Leu Gly Ser Arg Leu Tyr Ala Gln Thr Ala
                20                  25                  30

Asp Thr Gln Gln Trp Ile Asp Gly Ile Ala Ser Asn Met Gln Val His
            35                  40                  45

Tyr Gln Val Leu Leu Asn Lys Gly Asp Gly Glu Cys Ser Leu Pro Ser
        50                  55                  60

Leu Pro Pro Ser Pro Lys Ser Pro Cys Ser Ile Val Glu Leu Ser Leu
65                  70                  75                  80

Ser Ser Pro Asp Lys Leu Ala Ala Asn Asp Leu Asp Gly Asn Trp Ser
                85                  90                  95

Ile Tyr Phe Ser Gln Thr Asp Pro Ile Tyr Ala His Pro Ala Gly Glu
            100                 105                 110
```

-continued

```
Phe Thr Ile Asp His Ile Asn Gly Asp Leu His Arg Ile Arg Pro Ser
        115                 120                 125

Ala Ser Tyr Gln Gly Phe Asn Val Gly Glu Val Lys Lys Val Gln Phe
    130                 135                 140

Ile Val Ala Gly Leu Thr Leu Thr Glu Ala Lys Ile Met Pro Asn Tyr
145                 150                 155                 160

Tyr Val Val Ala Glu Gly Gln Asp Asn Lys Gln Ala Leu Tyr Ser Glu
                165                 170                 175

Ala Arg Val Ile Glu Ser Thr Arg Ile Arg Ile His Pro Glu Thr Gly
            180                 185                 190

Leu Glu Glu Arg Pro Phe Ala Gly Glu Ile Ser Arg Gln Asn Phe Lys
        195                 200                 205

Leu Ser Gln Ala Asp Lys Thr Pro Tyr Ala Asp Ala Phe Ile Phe
    210                 215                 220

Asn Glu Asn Lys Asn Val Asn Lys Leu Gly Phe Val Ala Gln Asp Glu
225                 230                 235                 240

Ala Leu Arg Thr Ile Ile Pro Thr Pro Thr Phe Val Met Asp Ser Gly
                245                 250                 255

Lys Asn Ile Asp Ile Ser Ala Gly Ile Asn Leu Gln Leu Gln Gly Val
            260                 265                 270

Glu Gln Asp Ala Val Ala Pro Ala Leu Ala Trp Leu Gln Ala Leu Gly
        275                 280                 285

Leu Lys Gln Asn Pro Ala Gly Met Pro Phe Val Val Ser Val Ser Arg
    290                 295                 300

Ala Ser Leu Pro Ser Arg Ser Pro Val Gly Ser Tyr Gln Leu Val Val
305                 310                 315                 320

Ser Pro Thr Gln Ile Thr Ile Phe Ala Arg Glu Pro Val Gly Ala Phe
                325                 330                 335

Tyr Gly Met Gln Ser Leu Ala Ser Val Met Ile Ala Gly Arg Asn Thr
            340                 345                 350

Leu Pro Val Leu Thr Val Asn Asp Ser Pro Arg Tyr Pro Tyr Arg Gly
        355                 360                 365

Met His Ile Asp Val Gly Arg Asn Phe His Ser Lys Gln Gln Ile Leu
    370                 375                 380

Asp Val Leu Asp Gln Met Ala Ala Tyr Lys Leu Asn Lys Leu His Leu
385                 390                 395                 400

His Leu Gly Glu Asp Glu Gly Trp Arg Leu Gln Ile Pro Ser Leu Pro
                405                 410                 415

Glu Leu Thr Asp Val Gly Gly Lys Arg Cys His Asp Pro Gln Glu Asn
            420                 425                 430

Thr Cys Leu Leu Met Gln Leu Gly Ala Asp Val Ser Gly Lys Ser Glu
        435                 440                 445

Arg Asp Gly Tyr Tyr Thr Arg Gln Asp Tyr Ile Glu Leu Val Lys Ala
    450                 455                 460

Ala Asn Ala Arg His Ile Gln Leu Ile Pro Ser Phe Asp Met Pro Gly
465                 470                 475                 480

His Ser Arg Ala Val Ile Lys Ala Met Glu Ala Arg Tyr Arg Lys Phe
                485                 490                 495

Met Ala Ala Gly Asn Lys Lys Ala Ala Glu Gln Tyr Leu Leu Ser Asp
            500                 505                 510

Pro Asn Asp Lys Thr Gln Tyr Lys Ser Ile Gln Phe Tyr Ser Asp Asn
        515                 520                 525

Thr Ile Asn Ala Cys Met Glu Ser Pro Tyr Lys Phe Leu Gly Lys Val
```

```
                    530             535             540
Ile Asp Glu Val Lys Ala Met His Ser Glu Ala Gly Gln Pro Leu Thr
545                 550             555                 560

Val Tyr His Ile Gly Ala Asp Glu Thr Ala Gly Ala Trp Ala Gln Ser
                565             570                 575

Pro Ile Cys Gln Ala Phe Phe Ala Asn Asn Pro Tyr Gly Val Glu Asn
                580             585                 590

Ala Lys Gln Leu Gly Ala Tyr Phe Ile Glu Arg Val Ala Ala Leu Leu
                595             600                 605

Glu Thr Lys Gly Ile Lys Thr Ala Gly Trp Ser Asp Gly Leu Ser His
                610             615                 620

Thr Asn Pro Lys Asn Met Pro Ala Lys Val Gln Ser Tyr Ile Trp Asp
625                 630             635                 640

Val Leu Pro Trp Gly Val Ala Glu Ala Asn Lys Gln Ala Asn Arg
                645             650                 655

Gly Trp Asp Val Val Leu Ser His Pro Asp Ala Leu Tyr Phe Asp Phe
                660             665                 670

Pro Tyr Glu Pro Asp Pro Lys Glu Gly Tyr Tyr Trp Gly Ser Arg
                675             680             685

His Ile Asp Thr His Lys Val Phe Asn Tyr Met Pro Gly Asn Leu Pro
                690             695             700

Ala Leu Ala Glu Val Tyr Pro Ser Pro Thr Gln Thr Gly Phe Glu Ile
705                 710             715                 720

Ala Gly Thr Thr Pro Leu Lys Gln Gly Val Gln Trp Ala Gly Ile Gln
                725             730                 735

Gly Gln Leu Trp Ser Glu Thr Ile Arg Ser Asp Asn Ala Val Glu Tyr
                740             745                 750

Met Ile Phe Pro Arg Leu Ile Ala Leu Ala Glu Arg Ala Trp His Ala
                755             760             765

Pro Ser Trp Glu Pro Pro Tyr Asn Tyr Glu Gly Ala Thr Tyr Asn Ala
                770             775             780

Asn Ser Gly Leu Phe Ser Glu Asn Lys Lys Ser Glu Arg Asp Lys Ala
785                 790             795                 800

Trp Leu Lys Phe Ala Ser Val Ile Gly Tyr Lys Glu Phe Val Lys Leu
                805             810                 815

Asp Ala Ala Asp Ile His Tyr Arg Ile Pro Thr Val Gly Ala Ile Ile
                820             825                 830

Gln Asp Ser Met Leu His Ala Asn Leu Ala Tyr Pro Gly Leu Gly Ile
                835             840             845

Glu Tyr Lys Glu Ala Gly Lys Asp Trp Gln Pro Tyr Asn Lys Pro Val
                850             855             860

Gln Val Lys Thr Pro Val Leu Val Arg Ala Lys Ala Ala Thr Gly Asp
865                 870             875                 880

Arg Lys Gly Arg Ala Leu Pro Val Glu
                885

<210> SEQ ID NO 16
<211> LENGTH: 344
<212> TYPE: PRT
<213> ORGANISM: Microbulbifer degradans

<400> SEQUENCE: 16

Met Leu Glu Thr Asn Asn Gln Leu Leu Gly Pro Val Ile Ala Asp Ile
1               5                   10                  15
```

```
Ala Gly Gln Thr Leu Ser Asp Glu Asp Ile Ala Leu Ile Lys Asn Pro
            20                  25                  30

Leu Ile Gly Gly Leu Ile Leu Phe Thr Arg Asn Tyr Ser Thr Pro Ser
        35                  40                  45

Gln Leu Asp Ala Leu Val Lys Gln Ile Arg Ser Val Arg Ala Asp Ile
     50                  55                  60

Ile Leu Ala Val Asp His Glu Gly Gly Arg Val Gln Arg Phe Arg Glu
 65                  70                  75                  80

Gly Phe Thr Arg Ile Pro Ala Met Gln Val Phe Ala Ser Ala Tyr Lys
                 85                  90                  95

Ala Arg Ala Glu Leu Thr Leu Ala Leu Ala Cys Asn Thr Gly Trp Leu
            100                 105                 110

Met Ala Ser Glu Leu Arg Ala Tyr Asp Ile Asp Ile Ser Phe Ala Pro
        115                 120                 125

Val Leu Asp Val Asp Asp Ser Phe Ser Ile Ile Gly Asp Arg Ala
    130                 135                 140

Phe Ser Ser Asp Pro Lys Ala Val Thr Ala Leu Ala Gly Ala Phe Ile
145                 150                 155                 160

Asp Gly Met Gln Gln Ala Gly Met Ala Cys Thr Gly Lys His Phe Pro
                165                 170                 175

Gly His Gly Ser Val Arg Ala Asp Ser His Leu Glu Leu Pro Val Asp
            180                 185                 190

Tyr Arg Ser Leu Glu Ala Ile Glu Gln Leu Asp Leu Met Pro Phe Ala
        195                 200                 205

Lys Leu Gln Ser Lys Leu Asp Ala Val Met Pro Ala His Ile Leu Phe
    210                 215                 220

Pro Glu Val Asp Asp Gln Pro Val Gly Phe Ser Ser Val Trp Leu Gln
225                 230                 235                 240

Lys Ile Leu Arg Asp Lys Met Ala Tyr Asp Gly Val Ile Phe Ser Asp
                245                 250                 255

Asp Leu Thr Met Glu Gly Ala Ala Val Ala Gly Ser Phe Gly Glu Arg
            260                 265                 270

Ala Ile Lys Ala Met Ser Ala Gly Cys Asp Thr Leu Leu Val Cys Asn
        275                 280                 285

Asn Arg Glu Ala Thr Leu Glu Val Ile Gln Thr Leu Ala Asp Asn Gly
    290                 295                 300

Asn Tyr Ser Thr Ser Ile Arg Leu Thr Arg Met Arg Gly Lys Ala Gly
305                 310                 315                 320

Ala Gln Pro Ile Tyr Asp Leu His Asn Asn Lys Arg Trp Gln Glu Thr
                325                 330                 335

Lys Glu Ala Leu Leu Ala Leu Ala
            340

<210> SEQ ID NO 17
<211> LENGTH: 462
<212> TYPE: PRT
<213> ORGANISM: Microbulbifer degradans

<400> SEQUENCE: 17

Asn Ala Gly Val Asp Ala Glu Leu Gly Tyr Ser Ile Gly Asp Val Tyr
 1               5                  10                  15

Ala Pro Ser Phe Asp Tyr Thr Ala Val Gly Gly Glu Arg Lys Thr Asp
            20                  25                  30

Asn Tyr Arg Val Ile Gly Tyr Tyr Met Pro Ser Leu Asp Gly Ser Phe
        35                  40                  45
```

-continued

```
Pro Pro Ser Ala Ile Gly Glu Gln Ala Gln Met Leu Thr His Ile
     50                  55                  60

Asn Tyr Ala Phe Ile Gly Ile Asn Ser Gln Leu Glu Cys Asp Phe Ile
 65                  70                  75                  80

Asp Val Glu Lys Ala Asp Ala Glu Thr Gln Ile Ala Glu Leu Gln
                 85                  90                  95

Ala Leu Lys Asn Trp Asn Ala Asp Leu Lys Ile Leu Phe Ser Val Gly
            100                 105                 110

Gly Trp Ala Glu Ser Asn Asp Ala Ala Glu Thr Val Ser Arg Tyr Arg
        115                 120                 125

Asp Ala Phe Ala Pro Ala Asn Arg Glu His Phe Val Ser Ser Cys Val
    130                 135                 140

Ala Phe Met Gln Gln His Gly Phe Asp Gly Ile Asp Ile Asp Trp Glu
145                 150                 155                 160

Tyr Pro Arg Ala Glu Asp Val Asp Asn Phe Ile Ala Gly Leu Ala Ala
                165                 170                 175

Met Arg Asn Gln Leu Asp Ala Arg Gly Asn Gly Glu Leu Val Thr Ile
            180                 185                 190

Ala Gly Ala Gly Gly Ala Phe Phe Leu Ser Arg Tyr Tyr Ser Lys Leu
        195                 200                 205

Ala Ala Ile Val Glu Gln Leu Asp Phe Ile Asn Leu Met Thr Tyr Asp
    210                 215                 220

Leu Asn Gly Pro Trp Asn Gly Val Thr Lys Thr Asn Phe His Ala His
225                 230                 235                 240

Leu Tyr Gly Asn Asn Gln Glu Pro Arg Phe Tyr Asn Ala Leu Arg Glu
                245                 250                 255

Ala Asp Leu Gly Leu Thr Trp Glu Glu Ile Val Glu Arg Phe Pro Ser
            260                 265                 270

Pro Phe Glu Leu Thr Val Asp Ala Ala Ile Lys Gln His Leu Met Met
        275                 280                 285

Asp Ile Pro Arg Glu Lys Ile Val Met Gly Val Pro Phe Tyr Gly Arg
    290                 295                 300

Ala Phe Phe Asn Thr Gly Ser Ser Asn Thr Gly Leu Tyr Gln Thr Phe
305                 310                 315                 320

Asn Thr Pro Asn Gly Asp Pro Tyr Val Gly Asp Ala Ser Leu Leu Val
                325                 330                 335

Gly Cys Glu Ala Cys Glu Ala Arg Gly Glu Pro Arg Ile Ala Thr Phe
            340                 345                 350

Asn Asp Ile Gln Gln Leu Ile Glu Gly Asn Tyr Trp Tyr Thr Arg His
        355                 360                 365

Phe Asp Asp Gln Thr Lys Ala Pro Trp Leu Tyr His Ala Glu Asn Asn
    370                 375                 380

Ile Phe Val Thr Tyr Asp Asp Ala Gln Ser Leu Val Tyr Lys Thr Asp
385                 390                 395                 400

Tyr Ile Lys Gln Gln Gly Leu Gly Gly Ala Met Phe His Leu Gly Gln
                405                 410                 415

Asp Asp Ser Gln Phe Thr Leu Leu Ala Thr Leu His Thr Glu Leu Asn
            420                 425                 430

Gly Ala Asn Ala Gly Ser Leu Gln Gly Gly Asn Ser Glu Thr Asp Asn
        435                 440                 445

Thr Thr Asp Glu Thr Glu Gly Asn Asn Glu Asp Asn Thr Glu
    450                 455                 460
```

<210> SEQ ID NO 18
<211> LENGTH: 1457
<212> TYPE: DNA
<213> ORGANISM: Microbulbifer degradans

<400> SEQUENCE: 18

```
tagttcatca tcaagctcta gtagctcaag ttcgtcttct agttcatcgt caagttcttc      60
aagctcttct agttcatcaa gcacgggcgg tggcaatgcg ggtgtagatg ccgaattggg     120
ttacagcatt ggcgacgtct atgcgccaag ctttgattac accgcagtag gcggcgagcg     180
caaaacagat aactaccgcg ttattggcta ttacatgcca agtttagatg gttcgtttcc     240
gcctagcgca attggtgagc aacaagcgca aatgcttacc catattaact atgcatttat     300
tggtattaac agccagctag agtgcgattt tatagatgta gaaaagccg acgcagaaac     360
tcaaattatt gctgagttac aagcactaaa aaattggaat gccgatttaa aaatccttt      420
ttctgtaggg ggttgggcag aatctaacga cgcagccgaa accgttagcc gctaccgcga     480
tgcgtttgca ccggcaaacc gcgagcattt tgttagctcg tgtgtagcct ttatgcaaca     540
acacggcttt gatggcatag atatagattg ggaataccct cgcgccgaag atgtagataa     600
ctttattgcc ggcctagcag caatgcgcaa ccaattggat gcacgcggca acggcgagct     660
agttaccatt gctggcgcag gcggtgcgtt cttttttaagc cgttattaca gcaagctagc     720
tgccatagta gaacagttag actttataaa tttaatgacc tacgacctaa acggaccgtg     780
gaacggcgta acaaaaacta actttcacgc acacctgtac ggcaacaacc aagagccgcg     840
cttttacaac gcgctgcgcg aagcagacct tggtttaacg tgggaagaaa tagtagagcg     900
ttttcctagc ccgttcgagc tcaccgtaga tgccgccatt aaacaacatt taatgatgga     960
tattccgcgc gaaaaaattg taatgggcgt accttttac ggtcgtgcat tttttaacac     1020
aggttcatca acaccggtt tataccaaac ctttaacacc ccaaatggtg acccctatgt     1080
aggtgacgct agcttattgg ttggttgtga agcctgcgaa gcgcgcggcg agccacgcat     1140
tgctaccttt aacgatattc aacaacttat agaaggtaac tacggctata cccgtcactt     1200
tgatgatcaa accaaagcgc cttggttgta tcacgcagaa aataatatat tgtaaccta     1260
cgacgatgct caatcgttgg tgtataaaac cgattatatt aaacaacaag gtttaggcgg     1320
tgcgatgttt tggcacctag ccaagatga ttcgcaattt actttattgg ctactttaca     1380
caccgagcta aacggcgcaa acgctggtag cctgcaaggt ggcaatagcg aaaccgacaa     1440
cacaacggac gaaacag                                                   1457
```

<210> SEQ ID NO 19
<211> LENGTH: 431
<212> TYPE: PRT
<213> ORGANISM: Microbulbifer degradans

<400> SEQUENCE: 19

```
Asp Leu Ser Gly Val Val Tyr Gly Glu Tyr Asn Asn Thr Tyr Lys Gln
 1               5                  10                  15

Thr Ser Asp Lys Ile Ile Val Thr Tyr Phe Val Glu Trp Gly Ile Tyr
             20                  25                  30

Gly Arg Asp Tyr His Val Asn Asn Ile Pro Ala Ser Asn Leu Thr His
         35                  40                  45

Val Leu Phe Gly Phe Ile Ala Met Cys Gly Asp Asn Pro His Ala Ser
     50                  55                  60

Gly Gly Ala Gln Ala Ala Ile Ala Ser Glu Cys Ala Asp Lys Gln Asp
```

|     |     |     |     |     | 65  |     |     |     |     | 70  |     |     |     |     | 75  |     |     |     |     | 80  |
| --- | --- | --- | --- | --- | --- | --- | --- | --- | --- | --- | --- | --- | --- | --- | --- | --- | --- | --- | --- | --- |

Phe Glu Val Thr Leu Val Asp Arg Phe Ala Asn Leu Glu Lys Thr Tyr
                85                          90                          95

Pro Gly Asp Thr Trp Tyr Asp Thr Thr Gly Gln Asp Tyr Asn Gly
            100                         105                         110

Asn Phe Gly Gln Leu Arg Lys Leu Lys Ala Gln His Pro His Leu Lys
            115                         120                         125

Ile Leu Pro Ser Ile Gly Gly Trp Thr Met Ser Thr Pro Phe Tyr Glu
130                         135                         140

Met Ala Lys Asn Glu Ala Asn Arg Ala Val Phe Val Glu Ser Ala Val
145                         150                         155                         160

Asn Phe Ile Lys Lys Tyr Asp Phe Phe Asp Gly Val Asp Ile Asp Trp
                165                         170                         175

Glu Tyr Pro Val Tyr Gly Gly Thr Ala Pro Glu Leu Ser Thr Ala Ala
            180                         185                         190

Asp Arg Asp Ala Tyr Thr Ala Leu Met Arg Asp Leu Arg Ala Ala Leu
            195                         200                         205

Asp Glu Leu Ala Glu Glu Thr Gly Arg Glu Tyr Glu Ile Thr Ser Ala
210                         215                         220

Val Gly Ala Ala Pro Glu Lys Ile Ala Ala Val Asp Tyr Ala Ser Ala
225                         230                         235                         240

Thr Thr Tyr Met Asp Tyr Ile Phe Leu Met Ser Tyr Asp Tyr Met Gly
                245                         250                         255

Ala Trp Ala Asn Thr Thr Gly His His Thr Pro Leu Tyr Asn Asn Asn
            260                         265                         270

Glu Glu Arg Glu Gly Phe Asn Thr His Ala Ser Val Gln Asn Leu Leu
            275                         280                         285

Thr Ala Gly Val Pro Ser Ser Lys Leu Val Val Gly Gly Ala Phe Tyr
290                         295                         300

Gly Arg Gly Trp Val Gly Thr Gln Asn Thr Asn Ala Ala Lys Ser Asp
305                         310                         315                         320

Leu Phe Pro Leu Tyr Gly Gln Ala Ser Gly Ala Ala Lys Gly Thr Trp
                325                         330                         335

Glu Ala Gly Val Gln Asp Tyr Arg Asp Leu Tyr Asp Asn Tyr Ile Gly
            340                         345                         350

Thr Asn Gly Thr Gly Ile Asn Gly Phe Ser Ala His Tyr Asp Glu Ile
            355                         360                         365

Ala Glu Ala Ala Tyr Leu Trp Asn Ser Ser Thr Gly Glu Phe Ile Ser
370                         375                         380

Tyr Asp Ser Pro Arg Ser Ile Ala Ala Lys Ala Asp Tyr Val Lys Gln
385                         390                         395                         400

Tyr Asn Leu Ala Gly Met Leu Thr Trp Glu Ile Asp Gly Asp Asn Gly
                405                         410                         415

Gln Leu Leu Asn Ala Ile Asn Glu Ser Phe Gly Asn Glu Lys Gln
            420                         425                         430

<210> SEQ ID NO 20
<211> LENGTH: 1305
<212> TYPE: DNA
<213> ORGANISM: Microbulbifer degradans

<400> SEQUENCE: 20
ggcgaaacag atttatctgg cgtggtttac ggcgagtaca acaacactta caaacagacg    60
agcgataaaa taattgttac ttactttgta gagtggggca tttatggccg cgactatcac   120

-continued

```
gtaaataata ttccggcgtc taaccttacg cacgtactgt ttggctttat tgcaatgtgt      180
ggcgataacc cacacgcctc aggcggcgcg caagcggcta ttgctagcga gtgtgcagat      240
aagcaagatt ttgaagttac cttggtagat cgtttcgcca acctagaaaa aacttaccca      300
ggcgatacgt ggtacgacga tacaaccggt caagattaca atggtaactt tgggcaacta      360
cgcaaactaa aagcacagca cccgcattta aaaatattgc catctattgg cggctggaca      420
atgtctaccc cattttatga aatggcaaaa aatgaagcta accgcgcagt gtttgttgaa      480
tctgccgtta actttattaa aaaatatgac ttcttcgacg gagtagatat agattgggaa      540
taccctgtat acggcggtac agccccagaa ttatctaccg ctgccgaccg cgatgcctat      600
accgccttaa tgcgtgacct acgcgcagca ttagacgagc tggcagaaga aacgggtcgc      660
gaatacgaaa ttacttcggc cgtaggtgca gcaccagaaa aaattgcagc agtagattac      720
gccagtgcca caacgtatat ggattacata ttcctaatga gctacgacta catgggcgca      780
tgggcgaaca caacgggtca ccacaccccg ctgtacaaca caacgaaga gcgagaaggt      840 tttaacacac atgcgtctgt gcaaaaccta ttaaccgcag gtgtgccttc atccaaatta      900
gtcgtgggtg gtgcattcta cggccgcggc tgggtaggca cccaaaatac caacgctgcc      960
aaaagcgatt tattcccgct atatggccaa gcttctggcg cggcaaaagg cacctgggaa     1020
gcaggggtac aagactaccg cgacctgtac gacaactata ttggcaccaa tggcacaggc     1080
attaatggct ttagcgcaca ctacgacgaa atagccgaag ccgcctacct ttggaacagc     1140
agcaccggcg aatttataag ctacgattcg ccgcgctcta ttgcagcaaa agccgattac     1200
gtaaaacaat acaatctagc tggcatgcta acctgggaaa tagacggcga taacggccaa     1260
ctactcaacg ccattaacga aagtttcggc aacgaaaagc agtag                      1305
```

```
<210> SEQ ID NO 21
<211> LENGTH: 22
<212> TYPE: PRT
<213> ORGANISM: Artificial Sequence
<220> FEATURE:
<223> OTHER INFORMATION: Description of Artificial Sequence: Synthetic
      amino acid linker

<400> SEQUENCE: 21

Thr Glu Glu Thr Glu Thr Glu Thr Glu Thr Glu Thr Glu Thr Glu Thr
  1               5                  10                  15

Glu Thr Glu Thr Glu Thr
             20

<210> SEQ ID NO 22
<211> LENGTH: 14
<212> TYPE: PRT
<213> ORGANISM: Microbulbifer degradans

<400> SEQUENCE: 22

Glu Pro Glu Pro Glu Pro Glu Pro Glu Pro Glu Pro Glu Pro
  1               5                  10
```

CHITIN DEGRADATIVE SYSTEMS

CROSS-REFERENCE TO RELATED APPLICATIONS

This claims priority to U.S. Provisional Application No. 60/483,135, filed Jun. 27, 2003 and U.S. Provisional Application No. 60/483,383, filed Jun. 27, 2003, the contents of which are incorporated herein, in their entirety, by reference.

This invention was made with government support under Contract Number SA7528051E awarded by the NOM Sea Grant. The government has certain rights in the invention.

BACKGROUND OF THE INVENTION

1. Field of the Invention

The invention is generally directed to degradative enzyme systems. In particular, the present invention is directed to chitin depolymerases and associated proteins and enzymes found in *Microbulbifer degradans*.

2. Background of the Invention

Chitin, a homopolymer of repeating units of β-1,4-linked N-acetyl-D-glucosamine (GlcNAc), is the second most abundant polymer in the biome. It is found in various forms throughout the marine environment and is a component of crustacean and insect exoskeletons, yeast and fungal cell walls, and diatoms. Chitin is usually at least 90% acetylated and is often in a complex with proteins and other carbohydrates. The microcrystalline structure of chitin varies between antiparallel sheets (alpha chitin), parallel sheets (beta chitin), and a mixture of both (gamma chitin). Alpha chitin is found in the calyces of hydrozoa, mollusks, plankton, and as a component of the cuticles of arthropods. Beta chitin, a less stable and more degradable form of chitin, is found in mollusks, squid pen, diatoms, and insect exoskeletons and cocoons, and is the major component of fungal cell walls.

*Microbulbifer degradans* strain 2-40 is a marine γ-proteobacterium that was isolated from decaying *Sparina alterniflora*, a salt marsh cord grass in the Chesapeake Bay watershed. Consistent with its isolation from decaying plant matter, *M. degradans* strain 2-40 is able to degrade many complex polysaccharides, including cellulose, pectin, xylan, and chitin, which are common components of the cell walls of higher plants. *M. degradans* strain 2-40 is also able to depolymerize algal cell wall components, such as agar, agarose, and laminarin, as well as protein, starch, pullulan, and alginic acid. In addition to degrading this plethora of polymers, *M. degradans* strain 2-40 can utilize each of the polysaccharides as the sole carbon source. Therefore, *M. degradans* strain 2-40 is not only an excellent model of microbial degradation of insoluble complex polysaccharides (ICPs) but can also be used as a paradigm for complete metabolism of these ICPs. ICPs are polymerized saccharides that are used for form and structure in animals and plants. They are insoluble in water and therefore are difficult to break down.

Chitin is a difficult substrate for microbial degradation because it is usually crystalline and complexed with protein, salts, and other carbohydrates. Chitin is resistant to chemical degradation and is difficult to digest enzymatically because of the multiple steps required to expose and cleave the polymer. Because chitin resists chemical and physical breakdown, microorganisms must play a major role in its degradation. Many microorganisms have developed efficient strategies for the depolymerization, transport, and metabolism of chitin and its derivatives. These systems involve multiple enzyme activities, usually encoded on separate polypeptides. For example, *Pseudoalteromonas* strain S91, *Serratia marcescens*, and *Streptomyces coelicolor* secrete several chitin-depolymerizing enzymes in the presence of chitin. Surprisingly, almost no free chitin is found in marine sediments, demonstrating the efficiency of these microbial systems. Therefore, chitin represents an abundant source of carbon and nitrogen to microorganisms in the marine environment.

The glycoside hydrolase family 18 (GH18) domain is the most common catalytic domain of microbial chitin depolymerases. Despite sharing a consensus sequence and a conserved catalytic glutamic acid residue, GH18 domains differ in their activity toward polymeric chitin and chito-oligosaccharides (i.e., endo- versus exo-activity). Chitodextrinases, which depolymerize chitooligosaccharides but not chitin, also contain GH18 domains. Chitinolytic enzymes with GH18 domains have been isolated from organisms as diverse as psychrophilic eubacteria and hyperthermophilic archaeons, demonstrating the wide range of conditions to which these domains have adapted. Because conserved residues are found in GH18 domains with divergent optima and substrate specificities, sequence analysis is insufficient to determine the enzymatic specificities of newly discovered chitinases.

Endo- and exo-chitinases that function cooperatively to depolymerize chitin are known. Endochitinases randomly cleave glycosidic linkages, generating free ends and long chitooligosaccharides. These are then acted upon by exo-chitinases that release chitobiose from the non-reducing ends of each. While exo- and endo-chitinases are not able to depolymerize chitin alone, the presence of both activities significantly increases the efficiency of chitinolytic systems.

Therefore, there exists a need to identify enzyme systems that use chitin as a substrate, express the genes encoding the proteins using suitable vectors, identify and isolate the amino acid products (enzymes and non-enzymatic products), and use these products as well as organisms containing these genes to degrade plant and animal waste.

SUMMARY OF THE INVENTION

One aspect of the present invention is directed to systems that degrade plant and animal waste.

A further aspect of the invention is directed to a method for the degradation of substances comprising insoluble complex polysaccharides. The method involves breaking at least one bond between glucosamine units in chitooligosaccharides by applying a composition comprising at least one polypeptide that binds to the chitooligosaccharides.

Another aspect of the present invention is directed to groups of enzymes that catalyze reactions involving chitin or chitooligosaccharides.

Another aspect of the present invention is directed to polynucleotides that encoding polypeptides with chitin depolymerase activity, chitodextrinase activity, N-acetyl-D-glucosaminidase activity, or chitin binding activity.

A further aspect of the invention is directed to chimeric genes and vectors comprising genes that encode polypeptides with chitin depolymerase activity, chitodextrinase activity, N-acetyl-D-glucosaminidase activity, or chitin binding activity.

A further aspect of the invention is directed to polypeptides comprising at least two domains, in which the domains are separated by a poly-amino acid linker.

Another aspect of the invention is directed to the treatment of asthma by administering an effective amount of at least one compound made from the application of a composition comprising at least one of SEQ ID NO:1, SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:19 to chitin.

A further aspect of the invention is directed to a method for the identification of a nucleotide sequence encoding a polypeptide comprising any one of the following activities from *M. degradans*: chitin depolymerase, chitodextrinase, N-acetyl-D-glucosaminidase, or chitin binding. An *M. degradans* genomic library is constructed in *E. coli* and screened for the desired activity. Transformed *E. coli* cells with specific activity are created and isolated.

Other aspects, features, and advantages of the invention will become apparent from the following detailed description, which when taken in conjunction with the accompanying figures, which are part of this disclosure, and which illustrate by way of example the principles of this invention.

DETAILED DESCRIPTION

The degradation and metabolism of chitin by marine microorganisms appear to involve the synergistic action of multiple proteins, including several extracellular chitin depolymerases, non-catalytic chitin-bonding proteins, chitodextrinases, and periplasmic and cytoplasmic N-acetylglucosaminidases (chitobiases and N-acetylhexosaminidases). These proteins typically include conserved modules that function as catalytic domains or chitin-binding domains and also contain domains of unknown function such as fibronectin type III and/or polycystic kidney disease (PKD) domains. Many of the genes for these enzymes have been cloned individually from chitin-degrading organisms.

*M. degradans* is unique among marine bacteria in its ability to degrade more than 10 ICPs. The draft genome sequence reveals over 130 putative carbohydrases involved in the degradation of these ICPs. Forty-six of these proteins contain poly-amino acid linkers, which are generally limited to secreted enzymes involved in ICP degradation. The majority of the amino acids in these linkers are serines. This finding strongly suggests the importance of poly-amino acid linker motifs in carbohydrate catalysis in nature.

*M. degradans* strain 2-40 efficiently metabolizes chitin, among many other ICPs. *M. degradans* strain 2-40 degrades and metabolizes chitin by expression of extracellular, periplasmic, and cytoplasmic systems for the depolymerization, transport, and metabolism of chitin-derived products. The chitinolytic system of *M. degradans* strain 2-40 includes at least three chitin depolymerases (ChiA, ChiB, and ChiC), a non-catalytic chitin-binding protein (CbpA), a chitodextrinase (CdxA), and three N-acetylglucosaminidases (HexA, HexB, and HexC). The proteins of this system contain domains similar to catalytic and binding regions of other microbial chitinases and in some cases polyserine- and hydroxyl-amino acid-rich linkers of unknown function.

Chitin depolymerases are enzymes that causes the cleavage of the β-1,4-linkage between N-acetyl-D-glucosamine units. Chitin binding proteins are proteins that can bind to chitin. Chitodextrinases are proteins that are able to degrade soluble chitooligosaccharides but not polymeric chitin. N-acetylglucosaminidases are proteins that are able to cleave chitobiose to form two GlcNAcs.

Figure 1:
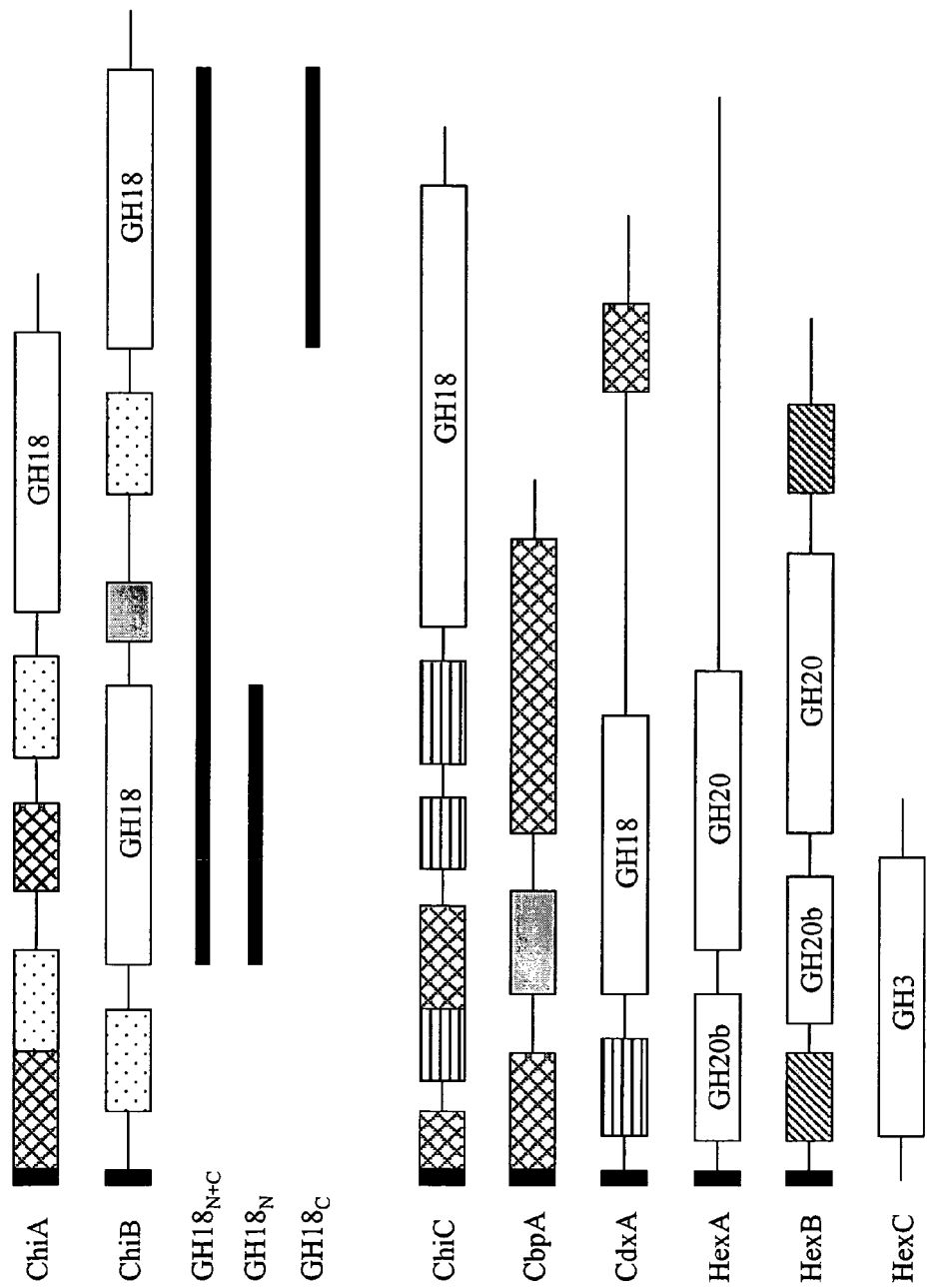
FIG. 1 shows poly-amino acid linkers, glutamic acid-rich domains, and conserved modules found in several polypeptides from *M. degradans*.

FIG. 1 shows various domains in ChiA, ChiB, ChiC, CbpA, CdxA, HexA, HexB, and HexC, which were isolated from *M. degradans* and expressed in *E. coli* according to the procedures described in Howard et al. (*J. Bacteriol.* 185(11), 3352-3360, 2003), the contents of which are herein incorporated in their entirety by reference. Protein sequence analysis of these proteins revealed the presence of putative type II secretion signals (black boxes); GH18, GH20, and GH3 domains; poly-amino acid domains (dotted boxes), chitin-binding domains (cross-hatched boxes); glutamine acid-rich domains (grey boxes); carbohydrate-binding domains; PKD domains (boxes with horizontal lines); soluble sugar-binding domains (hatched boxes); and conserved modules found in other microbial chitinases. FIG. 1 also shows the two domains of ChiB (black bars). $GH18_N$ is located between amino acids 221 and 605 of ChiB. $GH18_C$ is located between amino acids 860 and 1254.

The chiA (SEQ ID NO: 9) gene has 1632 base-pairs. The chiB (SEQ ID NO: 2) gene has 3186 base-pairs. The chiC (SEQ ID NO: 3) gene has 2379 base-pairs. The cbpA (SEQ ID NO: 4) gene has 1347 base-pairs. The cdxA (SEQ ID NO: 5) gene has 3441 base-pairs. The hexA (SEQ ID NO: 6) gene has 2388 base-pairs. The hexB (SEQ ID NO: 7) gene has 2670 base-pairs. The hexC (SEQ ID NO: 8) gene has 1035 base-pairs.

ChiA (SEQ ID NO: 1) is a 543-amino-acid protein with a calculated mass of 57.0 kDa. ChiA comprises two Cbd3 motifs and a GH18 domain. The first Cbd3 consisted of 46 residues and was most similar to a Cbd3 of ChiA from *Pseudoalteromonas* sp. strain S91. The sequence of the second 47-amino-acid domain was similar to the Cbd3 sequence from ChiA of *Vibrio cholerae*. The 299-amino-acid GH18 domain exhibited the highest identity with the GH18 domain of ChiA from *V. cholerae*. ChiA is composed of two amino-terminal chitin binding domains separated by a poly-amino acid linker. The second binding domain is followed by an additional poly-amino acid linker and a GH18 catalytic domain.

ChiB (SEQ ID NO: 10) is a modular, 1,271-amino-acid enzyme with a calculated molecular mass of 136.1 kDa. The amino terminus is predicted to contain a secretion signal that is separated from the remainder of the protein by a poly-amino acid linker of 148 amino acids, 99 of which are serine residues. ChiB includes two complete GH18 domains—an amino-terminal domain $GH18_N$ and a carboxy-terminal domain $GH18_C$—separated by a 180-amino-acid linker domain which includes an acidic region consisting of TE-$(ET)_{10}$ (SEQ ID NO: 21) and another poly-amino acid linker containing 39 serine residues. Both GH18 domains of ChiB are catalytically active but differentially cleave glycosidic linkages, depending on their location within the chitin polymer. In addition, chitin depolymerization is enhanced by the presence of both domains.

Figure 2:
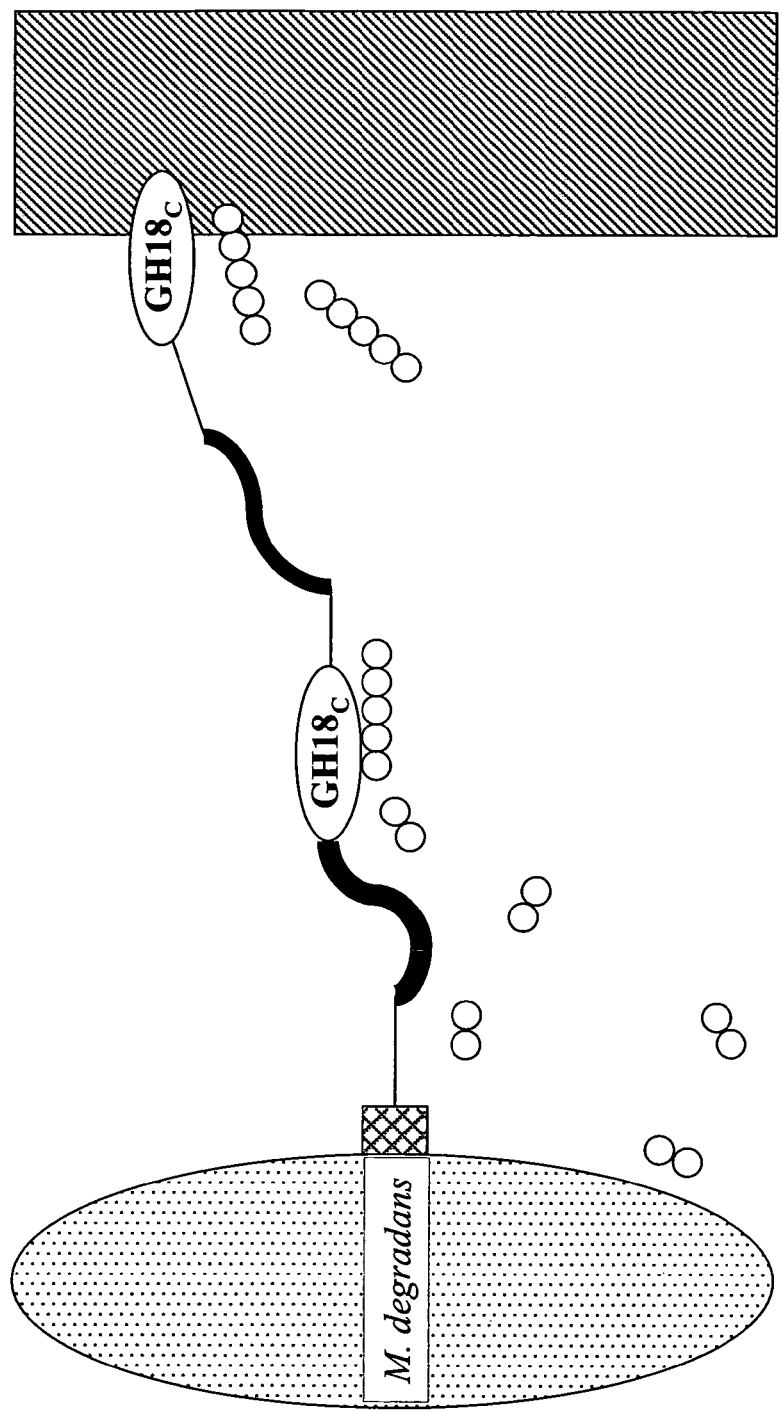
FIG. 2 shows a model for the chitin depolymerization of ChiB.

One of the catalytic domains of ChiB functions as an endochitinase while the other functions as an exochitinase, as shown in FIG. 2. ChiB is the first eubacterial chitinase demonstrated to contain two functional GH18 catalytic domains. The lack of carbohydrate binding domains and typical accessory domains (e.g., Fibronectin Type III domains, PKD domains) coupled with the discrete activities of each catalytic domain emphasize the novelty of this enzyme.

When expressed as separate polypeptides, each GH18 domain of ChiB was able to depolymerize chitin in zymograms and was most active under similar temperature, pH, and ionic conditions. A detailed description of the procedures used for chitin degradation analysis can be found in Howard et al. (*J. Bacteriol.* 186(5), 1297-1303, 2004), the contents of which are herein incorporated in their entirety by reference.

$GH18_N$ (SEQ ID NO: 17) is a 485 amino-acid protein (between amino acids 221 and 605 of ChiB), encoded by SEQ ID NO: 18 (1455 base-pairs; base-pairs 468 to 1924 of chiB). $GH18_N$ is more active on MUF-diNAG than MUF-triNAG and displayed a pattern of activity typical of an exo-chitinase on chitooligosaccharides. Chitobiose was released from the non-reducing end of $GlcNAc_4$-$GlcNAc_6$.

$GH18_C$ (SEQ ID NO: 19) is a 429 amino-acid protein (between amino acids 860 and 1254 of ChiB), encoded by SEQ ID NO: 20 (287 base-pairs; base-pairs 2512-3800 of chiB). $GH18_C$ releases MUF most rapidly from MUF-triNAG and is able to cleave chitooligosaccharides at multiple linkages, demonstrating endo-chitinase activity. $GH18_C$ is more than twice as active on native chitin as $GH18_N$. This is likely because native chitin has a paucity of free, exposed, ends. Therefore, exochitinases have far fewer sites at which they can act as compared to random cutting endochitinases that can cleave virtually any glycosidic linkage in the polymer.

The synergistic degradation of chitin observed when both domains were present further supports their proposed function. The presence of both domains on separate polypeptides increased the release of reducing sugars 140% over the theoretical combined rate calculated if the domains were only to act additively. This synergism would not be observed if both domains had the same activity.

Carbohydrases with two catalytic domains are rare among prokaryotes. Only a small number have been characterized, mostly from ruminants and thermophiles. For example, *Ruminococcus flavefaciens* 17 and *Fibrobacter succinogenes* S85, produce xylanases with two catalytic domains, though the latter appears to encode a xylanase with two domains of the same function. Two extreme thermophiles, *Anaerocellum thermophilum* (a γ-subgroup proteobacterium) and *Thermococcus kodakaraensis* KOD1 (an archeon), produce enzymes with two catalytic domains. *A. thermophilum* produces a cellulase with separate GH9 and GH48 domains that encode for endo- and exo-glucanase activity, respectively. A chitinase from *T. kodakaraensis*, Tk-ChiA, was shown to have an amino-terminal exochitinase domain, while the carboxy-terminus contains an endo-chitinase domain. Unlike ChiB of *M. degradans*, this enzyme also contains chitin-binding domains and is not predicted to anchor to the cell surface. Further, the exolytic domain of Tk-ChiA is able to weakly cleave the third glycosidic linkage from the non-reducing end of free chitin chains, an activity not observed in experiments with $GH18_N$.

The dual catalytic domains of ChiB function cooperatively to degrade chitin to chitobiose. Though maximal depolymerization was achieved when the catalytic domains of ChiB were on separate polypeptides, there are benefits to their presence as a single unit.

First, a single promoter region is able to regulate the expression of two enzymatic activities. This permits two essential components of the chitinolytic system to be simultaneously regulated from a single locus, much like an operon regulating genes encoding a polycistronic mRNA. However, unlike an operon where several individual proteins are produced, a single enzyme is encoded. The amount of energy and secretion machinery needed to deliver two enzymatic functions to the exterior of the cell is therefore decreased.

Second, encoding both activities on a single polypeptide ensures the proximity of the two domains during the in situ depolymerization of chitin. This allows for a synergistic and focused degradation of the polymer. In the environment, secreted enzymes diffuse away from their intended targets and not be available to assist other components of a degradative system. This is partially solved by the presence of carbohydrate binding domains (which appear to be lacking from ChiB), but there is no assurance that both endo- and exo-acting enzymes will bind to the same location and have the opportunity to act in concert to achieve the full potential of the system unless linked on a single polypeptide.

When both domains were present on the same polypeptide, the synergism between the domains was less apparent. The activity detected when the domains are joined was only a modest increase over the theoretical activity when compared to the activity of the two catalytic domains as separate entities. The decreased activity of the domains when linked may be the result of the domains then moving as a single protein as each encounters substrate. For example, as the exolytic domain is cleaving soluble chitooligosaccharides away from the insoluble polymer, the endolytic domain is unable to contact, and therefore degrade, its primary substrate. The amount of reducing sugars released would increase if the domains were free to act at different locations. Such an arrangement is of less benefit in nature where substrates are much more limited and less often encountered than in laboratory reactions.

A model of ChiB activity is shown in FIG. 2. ChiB likely attaches to a surface of a cell via a lipoprotein anchor (cross-hatched box). Activity of the endochitinolytic $GH18_C$ (oval) releases chitooligosaccharides from polymeric chitin (hatched box). Free chitooligosaccharides (small circles) are then acted upon by the exochitinolytic $GH18_N$ (oval) that processively releases chitobiose from the non-reducing end. Free chitobiose would then be taken up by the cell and metabolized. The poly-amino acid linkers (black "S"-shapes) may provide flexibility to the enzyme and optimize interaction with substrates.

Each catalytic site has been shown to be independently active, so the linkage between the domains prevents interference between them during the degradation of chitin. The processive cutting nature of exochitinases and random cutting behavior of endochitinases is applied to the activity model of ChiB. As $GH18_C$ releases chitooligosaccharides from the polymer, they can be immediately acted upon by $GH18_N$ which processively cleaves chitobiose from the non-reducing end. The lipoprotein acylation site present at the amino terminus of ChiB likely functions to anchor the enzyme to the outer membrane. This notion is strengthened by the observation that chitinase activity has been associated with outer membrane preparations of *M. degradans*. The membrane anchorage keeps two critical enzymatic activities in close proximity to the cell and forgoes the necessity of chitin-binding domains. The catalytic domain arrangement within ChiB allows chitooligosaccharides released by the activity of the distal $GH18_C$ to be transferred to the exo-acting domain, which is in close proximity to the outer membrane where newly formed chitobiose can be taken up by the cell. ChiB is found in crude membrane preparations of *M. degradans*.

ChiC (SEQ ID NO: 11) is a 792-amino-acid polypeptide with a calculated molecular mass of 87.1 kDa. ChiC had two Cbd3 domains. The first, a 46-amino-acid domain, is most similar to the Cbd3 of ChiB from *Vibrio harveyi*. The second, consisting of 49 amino acids, is most similar to the Cbd3 of ChiA from *V. cholerae*. ChiC also contained three PKD-like domains. ChiC had a 350-amino-acid C-terminal GH18 catalytic domain with strong similarity to ChiC from *Streptomyces peucetius*.

CbpA (SEQ ID NO: 12) is a 449-amino-acid polypeptide consisting of two carbohydrate binding domains but with no apparent catalytic domain. The first chitin-binding domain consisted of 220 amino acids and was most similar to the chitin-binding module of *P. aeruginosa* CbpD. The second was a 95-amino-acid type 2 carbohydrate-binding module with similarity to the CBM2 of a rhamnogalacturonan lyase from *Cellvibrio japonicus* (formerly *Pseudomonas cellulosa*). Similar chitin-binding proteins have been reported in a number of marine microorganisms, though their role in chitin degradation is poorly understood. It has been hypothesized that chitin-binding proteins keep a bacterium in close proximity to the chitin polymer to facilitate efficient degradation, though there is no direct evidence that these proteins bind both the cell and chitin simultaneously. A Glu-Pro-rich domain consisting of (Glu-Pro)$_7$ (SEQ ID NO: 22) is located between the carbohydrate-binding modules of CbpA.

CdxA (SEQ ID NO: 13) is a 1,088-amino-acid polypeptide, with a calculated molecular mass of 115.6 kDa, and comprises a typical type II-dependent secretion signal, two PKD domains, a 403-amino-acid GH18 catalytic site, and a 41-amino-acid Cbd3 chitin-binding domain. The GH18 domain is most similar to that of chitodextrinase ChiD from *Alteromonas* sp. strain O-7. The Cbd3 domain was most similar to the Cbd3 in *Pseudoalteromonas* sp. strain S91 ChiA.

HexA (SEQ ID NO: 14) is a 795-amino-acid polypeptide with a predicted molecular mass of 88.5 kDa. HexA carried a GH20 domain (glycosyl hydrolase family 20 catalytic domain 2) that is most similar to the active site of the *Alteromonas* sp. strain O-7 N-acetylhexosaminidase and a 348-aa GH20 domain related to the active site of the *Pseudoalteromonas* sp. strain S91 N-acetylglucosaminidase. HexA has an N-terminal type II-dependent secretion signal and may be a surface-anchored lipoprotein like ChiB.

HexB (SEQ ID NO: 15) is an 889-amino-acid polypeptide with a predicted mass of 98.4 kDa that contains a putative carbohydrate-binding domain, a GH20b domain found in the N-acetylhexosaminidase B of *Alteromonas* sp. strain O-7, and a 406-amino-acid GH20 domain identified as the active site of the N-acetylhexosaminidase of *Vibrio vulnificus*. HexB also contains an N-acetylhexosaminidase-like C-terminal domain related to the N-acetyl-D-glucosaminidase from *Enterobacter* sp. strain G-1. HexB also has an N-terminal type II-dependent secretion signal. The overall similarity of HexA and HexB to other N-acetylglucosaminidases and retention of key catalytic domains are consistent with their proposed activity.

HexC (SEQ ID NO: 16) is a 345-amino-acid polypeptide with a predicted mass of 37.4 kDa that lacks an apparent N-terminal secretion signal. Hex C has a GH3N domain (glycosyl hydrolase family 3 N-terminal domain) similar to that of *Pseudomonas aeruginosa* N-acetylglucosaminidase. HexC likely degrades cytoplasmic chitobiose. This activity could have a role in the regulation of genes activated by the presence of chitobiose and would also release GlcNAc for use as an energy source.

It is one aspect of the present invention to provide a nucleotide sequence that has a homology selected from 100%, 99%, 98%, 97%, 96%, 95%, 90%, 85%, 80%, or 75% to any one of SEQ ID NO:9, SEQ ID NO:2, or SEQ ID NO:3, having chitin depolymerase activity; SEQ ID NO:4, having chitin-binding protein activity; SEQ ID NO:5, having chitodextrinase activity, and any one of SEQ ID NO:6, SEQ ID NO:7, or SEQ ID NO:8, having N-acetylglucosaminidase activity. The present invention also covers replacement of between 1 and 20 nucleotides of any of SEQ ID NO:9, SEQ ID NO:2, SEQ ID NO:3, SEQ ID NO:4, SEQ ID NO:5, SEQ ID NO:6, SEQ ID NO:7, or SEQ ID NO:8 with non-natural or non-standard nucleotides for example phosphorothioate, deoxyinosine, deoxyuridine, isocytosine, isoguanosine, ribonucleic acids including 2-O-methyl, and replacement of the phosphodiester backbone with, for example, alkyl chains, aryl groups, and protein nucleic acid (PNA).

It is another aspect of the present invention to provide a nucleotide sequence that hybridizes to any one of SEQ ID NO:9, SEQ ID NO:2, SEQ ID NO:3, SEQ ID NO:4, SEQ ID NO:5, SEQ ID NO:6, SEQ ID NO:7, or SEQ ID NO:8 under a stringency condition of 1×SSC. It is another aspect of the present invention to provide a nucleotide sequence that hybridizes to any one of SEQ ID NO:9, SEQ ID NO:2, SEQ ID NO:3, SEQ ID NO:4, SEQ ID NO:5, SEQ ID NO:6, SEQ ID NO:7, or SEQ ID NO:8 under a stringency condition of 2×SSC. It is another aspect of the present invention to provide a nucleotide sequence that hybridizes to any one of SEQ ID NO:9, SEQ ID NO:2, SEQ ID NO:3, SEQ ID NO:4, SEQ ID NO:5, SEQ ID NO:6, SEQ ID NO:7, or SEQ ID NO:8 under a stringency condition of 3×SSC. It is another aspect of the present invention to provide a nucleotide sequence that hybridizes to any one of SEQ ID NO:9, SEQ ID NO:2, SEQ ID NO:3, SEQ ID NO:4, SEQ ID NO:5, SEQ ID NO:6, SEQ ID NO:7, or SEQ ID NO:8 under a stringency condition of 4×SSC. It is another aspect of the present invention to provide a nucleotide sequence that hybridizes to any one of SEQ ID NO:9, SEQ ID NO:2, SEQ ID NO:3, SEQ ID NO:4, SEQ ID NO:5, SEQ ID NO:6, SEQ ID NO:7, or SEQ ID NO:8 under a stringency condition of 5×SSC. It is another aspect of the present invention to provide a nucleotide sequence that hybridizes to any one of SEQ ID NO:9, SEQ ID NO:2, SEQ ID NO:3, SEQ ID NO:4, SEQ ID NO:5, SEQ ID NO:6, SEQ ID NO:7, or SEQ ID NO:8 under a stringency condition of 6×SSC. It is another aspect of the present invention to provide a nucleotide sequence that hybridizes to any one of SEQ ID NO:9, SEQ ID NO:2, SEQ ID NO:3, SEQ ID NO:4, SEQ ID NO:5, SEQ ID NO:6, SEQ ID NO:7, or SEQ ID NO:8 under a stringency condition of 7×SSC. It is another aspect of the present invention to provide a nucleotide sequence that hybridizes to any one of SEQ ID NO:9, SEQ ID NO:2, SEQ ID NO:3, SEQ ID NO:4, SEQ ID NO:5, SEQ ID NO:6, SEQ ID NO:7, or SEQ ID NO:8 under a stringency condition of 8×SSC. It is another aspect of the present invention to provide a nucleotide sequence that hybridizes to any one of SEQ ID NO:9, SEQ ID NO:2, SEQ ID NO:3, SEQ ID NO:4, SEQ ID NO:5, SEQ ID NO:6, SEQ ID NO:7, or SEQ ID NO:8 under a stringency condition of 9×SSC. It is another aspect of the present invention to provide a nucleotide sequence that hybridizes to any one of SEQ ID NO:9, SEQ ID NO:2, SEQ ID NO:3, SEQ ID NO:4, SEQ ID NO:5, SEQ ID NO:6, SEQ ID NO:7, or SEQ ID NO:8 under a stringency condition of 10×SSC.

It is another aspect of the present invention to provide a nucleotide sequence that encodes a polypeptide having chitin depolymerase activity. It is yet another aspect of the present invention to provide a nucleotide sequence that encodes a polypeptide having chitin-binding ability. It is a further aspect of the present invention to provide a nucleotide sequence that encodes a polypeptide having N-acetylglucosaminidase activity. It is well understood that due to the degeneracy of the genetic code, an amino acid can be coded for by more than one codon. Therefore, the present invention encompasses all polynucleotides that code for any one of SEQ ID NO: 1; SEQ ID NO: 10; SEQ ID NO: 11; SEQ ID NO: 12; SEQ ID NO: 13; SEQ ID NO: 14; SEQ ID NO: 15; or SEQ ID NO: 16.

The scope of this invention covers natural and non-natural alleles of any one of SEQ ID NO: 1; SEQ ID NO: 10; SEQ ID NO: 11; SEQ ID NO: 12; SEQ ID NO: 13; SEQ ID NO: 14; SEQ ID NO: 15; or SEQ ID NO: 16. In a preferred embodiment of the present invention, alleles of any one of SEQ ID NO: 1; SEQ ID NO: 10; SEQ ID NO: 11; SEQ ID NO: 12; SEQ ID NO: 13; SEQ ID NO: 14; SEQ ID NO: 15; or SEQ ID NO: 16 comprise replacement of one, two, three, four, or five naturally occurring amino acids with similarly charged, shaped, sized, or situated amino acids (conservative substitutions). The present invention also covers non-natural or non-standard amino acids for example selenocysteine, pyrrolysine, 4-hydroxyproline, 5-hydroxylysine, phosphoserine, phosphotyrosine, and the D-isomers of the 20 standard amino acids.

Chitin degrading enzyme systems, including one or more enzymes or chitin-binding proteins, have a number of uses. In one embodiment, these systems can be used to degrade chitin to produce short chain chitooligosaccharides for use in medicine. These are therapeutic for those suffering from asthma, as indicated in Zhu et al., (Science 304, 1678-1679, 2004), the contents of which are incorporated herein, in their entirety, by reference.

Longer chain oligosaccharides have been shown to kill cancer cells and reduce blood pressure. In another embodiment, these systems are used to break down chitin into short chain sugars or beginning to break down crab shell waste to a form that other bacteria can use. This is a valuable feedstock for bioreactors or fertilizers. In another embodiment, these systems are used to de-glycosylate proteins in plants and animals that are involved in disease. Removal of such glycoslyation could be a therapy for crops or animals. The protein of interest can further be glycosylated with the appropriate sugars.

Chitin and chitosan can be used to absorb environmental pollutants and waste spills. The chitin could then be degraded by the chitin degrading systems of the present invention. Bacteria that can metabolize environmental pollutants and can degrade chitin could be used in bioreactors that degrade toxic materials. Such a bioreactor would be advantageous since there would be no need to add additional nutrients to maintain the bacteria—they would use chitin as a carbon source. Bacteria engineered to express the chitin degradative systems and metabolize environmental pollutants are one preferred embodiment of the present invention.

Chitin degrading enzyme systems can be supplied in dry form, in buffers, as pastes, paints, micelles, etc. Chitin degrading enzyme systems can also comprising additional components such as metal ions, chelators, detergents, organic ions, inorganic ions, additional proteins such as biotin and albumin.

Other embodiments of the present invention involve strategic placement of correctly folded proteins on the surface of a bacterial cell and the separation of catalytic domains in an enzyme. The genome sequence of this *M. degradans* revealed 46 proteins with large poly-amino acid domains. For example, ChiA and ChiB include long polyserine domains that appear to separate functional groups/catalytic domains.

Of the *M. degradans* genes identified that encoded proteins with poly-amino acid linkers, 18 contained a single poly-amino acid linker, while 28 had two or more. These poly-amino acid linkers have an average length of 39 residues and an average composition of 79% serine, 11% glycine, 7% threonine, and 3% alanine. Glycine residues are predominantly found immediately flanking tracts of polyserine sequence, and more than 80% of the poly-amino acid linkers have glycine residues at their start or terminus. Several of the poly-amino acid linkers also contain a single aspartic acid or cysteine residue. Though serine is a predominant residue within each poly-amino acid linker, none were identical in terms of exact residue composition or sequence. Each of the six codons for serine is used to encode serines within the poly-amino acid linkers. None of these codons is used preferentially, nor were any of them arranged in any obvious pattern or repeat.

Poly-amino acid linkers containing proteins were identified using protein sequences based upon the translated nucleotide sequences of 140 completed microbial genomes and, where possible, the 125 unfinished microbial genomes found at the NCBI microbial genome homepage. Non-redundant, annotated protein sequence databases were searched for poly-amino acid linker proteins using the PIR pattern/peptide match program at the Protein Information Resource server. The domain architecture of each poly-amino acid linker protein was analyzed using the Simple Modular Architecture Research Tool. Type II secretion signals were identified using the iPSORT program and lipoprotein acylation sites were identified at the DOLOP website.

All of the 46 *M. degradans* poly-amino acid linker proteins are carbohydrate depolymerizing enzymes, carbohydrate binding proteins, or proteins with similarity to known proteins involved in carbohydrate degradation. These include 2 chitinases, 8 cellulases, 10 pectate lyases, 5 xylanases, 3 mannanases, a rhamnogalacturonan lyase, an alginate lyase, and 16 proteins of unknown function. Among the 16 proteins for which no activity could be predicted, each has weak similarity to a known degradative enzyme or contains sequence similarity to known carbohydrate binding module [CBM] or catalytic domain. In cases where no sequence similarity was identified, the poly-amino acid linkers separated the proteins into segments large enough to contain presently unconfirmed catalytic sites or CBMs. Each of the 46 poly-amino acid linkers containing proteins contains a Type II secretion signal.

In *M. degradans*, poly-amino acid linkers separate predicted binding and/or catalytic domains. In nine proteins, a poly-amino acid linker immediately follows the secretion signal. All nine of these proteins contain an apparent lipoprotein acylation site, i.e. each has at least one positively charged residue within the first five amino acids, a hydrophobic stretch of 8 to 10 residues, and a lipobox containing the appropriately conserved amino acids, including a cysteine residue. In gram-negative bacteria, when the cysteine residue within a lipobox is acylated, the protein becomes anchored to the inner or outer membrane. In the present invention, poly-amino acid linkers separate anchoring domains from the remainder of a protein.

Forty-two of the 46 genes encoding poly-amino acid linker proteins are unique within the *M. degradans* genome sequence. The remaining four genes include two pairs of paralogs. The genes for two predicted pectate lyases (ZP_

00067834 and ZP_00067832) exhibit greater than 75% identity among a carbohydrate binding domain and a Fibronectin Type III domain, and more than 80% identity between sequences corresponding to catalytic domains. The nucleotide sequence corresponding to the similarly located poly-amino acid linkers is less than 20% identical. Likewise, two cellulases (ZP_00066178 and ZP_00068260) also appear to have significant similarity at the nucleotide level except for their poly-amino acid linkers. In *C. japonicus*, the genes for XylB and XylC are located in tandem in the genome and contain duplicate sequence at their amino-termini, which includes a poly-amino acid linker. Duplicated genes wherein one of the genes encoded a poly-amino acid linker and the other did not were not identified in either organism. Thus, it does not appear that a known method of transposition or a recent, repetitive duplication event generated poly-amino acid linkers.

Interestingly, eight of the *M. degradans* poly-amino acid linker proteins are most similar to *C. japonicus* enzymes wherein sequence, overall domain architecture, and poly-amino acid linker location are conserved. Horizontal transfer is known to play a role in the acquisition of new genetic material by bacteria, though it often occurs in specific eco-niches, such as the rumen. It is unlikely that *C. japonicus*, a soil bacterium, and *M. degradans*, a marine bacterium, have recently shared a common environment. Thus, these genes may have been exchanged before each evolved to different habitats or may have been inherited from a common ancestor. In either case, these domain arrangements have been conserved for an evolutionarily long period of time, suggesting that the placement of the domains and poly-amino acid linkers within each enzyme is functionally significant.

Beyond the poly-amino acid linker proteins of *M. degradans* and *C. japonicus*, 17 poly-amino acid linker proteins were identified during searches of the non-redundant database as well as complete and incomplete microbial genome sequences. No proteins with poly-amino acid linkers were identified among archeae. Cellulose degrading enzymes with poly-amino acid linkers were identified in *Pseudomonas* sp. ND137, *Xyella fastidiosa* strain Temecula1, *Xyella fastidiosa* strain 9a5c, and *Ruminococcus albus*. *Erwinia chrysanthemi* encodes OutD, a pectic enzyme secretion protein, that contains a poly-amino acid linkers. These species, however, do not encode more than one protein with a poly-amino acid linker.

There are several observations that suggest poly-amino acid linkers are flexible. First, using the NORSp program, poly-amino acid linkers are not predicted to have a regular secondary structure, but are instead extended, 'loopy' regions. Secondly, lipovitellin, a eukaryotic protein that contains a poly-amino acid (polyserine) region, was partially crystallized. The poly-amino acid linker region was, however, not included in the crystal structure. This is consistent with the notion that disordered regions are not amenable to crystallization. Finally, glycine residues flank >80% of the poly-amino acid linkers in *M. degradans* proteins. These residues may increase the overall flexibility of these regions, as the flexibility of glycine is well documented. Taken together, these factors suggest that poly-amino acid linkers are disorganized, flexible spacers.

During the degradation of ICPs, flexible linker regions coupling a catalytic and a binding domain could expand the potential substrate target area available to the enzyme after a CBM makes contact with a polymer. Similarly, poly-amino acid linkers could enhance substrate availability to an enzyme anchored to a bacterial outer membrane, a potential survival advantage in the marine environment where diffusion and dilution are major factors affecting extracellular enzymes. In nine *M. degradans* enzymes and in several hypothetical proteins from other organisms, poly-amino acid linkers are located immediately after an amino-terminal lipobox, suggesting that poly-amino acid linkers can function to extend the catalytic and/or binding domains of a surface associated enzyme from the outer membrane.

Based upon thorough searches of existing prokaryotic genome databases, the known enzymes of *C. japonicus*, searches of the non-redundant database, and the considerable data afforded by analysis of the *M. degradans* genome, it is likely that in prokaryotes, poly-amino acid linkers are generally found within secreted, complex polysaccharide depolymerizing enzymes or proteins involved in carbohydrate binding or metabolism in order to assist in interaction with substrates.

While *M. degradans* encodes 46 proteins with poly-amino acid linkers involved in complex carbohydrate degradation, it likely contains nearly twice that number of extracellular carbohydrases wherein the domains are not separated by repetitive linking sequence. Similarly, *C. japonicus* also encodes carbohydrases that do not contain poly-amino acid linkers. The deletion of poly-amino acid linkers from two *C. japonicus* xylanases decreased their activity on insoluble substrates, but does not altogether abolish their activity or reduce binding. Furthermore, threonine/proline rich linkers have been shown to be dispensable with only moderate loss of activity. These observations indicate that while poly-amino acids may not be required for carbohydrase function, they may have evolved to enhance the activity of certain enzyme configurations, particularly during in situ degradation of ICPs. Though poly-amino acid linker coding sequences are dynamic, their amino acid sequences are static, suggesting specific structural constraints associated with advantageous function.

Poly-amino acids also appear to function as linker regions between functional domains within enzymes and separate binding and catalytic domains. The average length of poly-amino acid linkers is 39 residues. They are composed mostly of serine (74%), but also contain alanine, threonine, and glycine. Another proposed function of these linkers is to provide additional space between functional modules, perhaps to allow for proper folding of the peptide and to allow a larger area to be accessed by the enzyme after it has bound a substrate.

In several of these proteins, the poly-amino acid linker separates catalytic or binding domains from an amino-terminal lipoprotein box. A lipoprotein box is likely used by γ-subgroup proteobacteria to anchor enzymes to the cell surface via an acylation of an internal cysteine. Being able to separate the lipoprotein box from the catalytic portions of a protein presents several advantages. First, functional domains are not in close proximity to the cell surface, which may interfere with protein folding and function, thus in one embodiment of the invention, the poly-amino acid linkers provide a mechanism to tether correctly folded proteins to the cell surface. Second, in another embodiment, the poly-amino acid linkers ensure that the catalytic portions of the protein are exposed to the extracellular environment and not trapped in the periplasm or outer membrane. In a third embodiment, the poly-amino acid linkers expand the length of the protein so that it can 'reach' further into the environment to contact substrates.

The lipid-anchored proteins of *M. degradans* with poly-amino acid linker domains have most likely evolved to function well on the outer membrane of a Gram-negative bacterial. Functional proteins in *E. coli* as a lipoprotein anchors, are excellent tools for arraying any known protein of interest on the surface of an *E. coli* cell, while allowing the protein of interest to retain a native (and active) conformation.

The poly-amino acid linker domains described here have been observed in at least two other bacteria: *Cellvibrio cellulose* and *Teridobacter* spp. In these organisms, the poly-amino acid linker domains are not observed at the extreme amino-terminus, nor are they found in predicted lipoproteins. The amount of additional space that would exist between the cell and any arrayed enzyme by virtue of the poly-amino acid linker domain suggests that a protein expressed with this amino-terminal motif assumes a native conformation once on the cell surface.

In one embodiment of the present invention, this type of amino-terminal modification is incorporated into the construction of a plasmid vector that can be used to create fusion proteins with peptides of interest. This type of vector could have significant use in the fields of bioengineering and proteomics. In another embodiment of the present invention, this vector would allow proteins to be presented and anchored to the surface of the cell. This would allow waste to be modified by presenting an enzyme on the surface of the cell and growing the waste material in culture with the *E. coli* expression strain. By centrifuging the reaction, modified (and possibly valuable) products can be collected that would be substantially free of both cells and enzyme. This is of particular interest to the bioprocessing and bioremediation fields. This system could be used to display epitopes on the surface of any Gram-negative bacterium for vaccine development.

Figure 3:
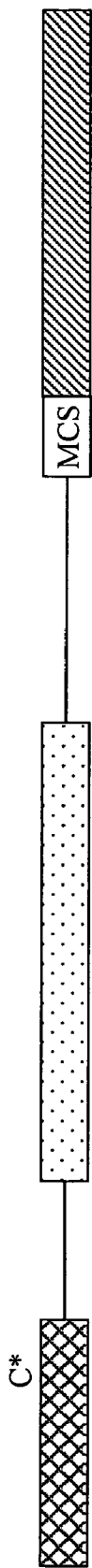
FIG. 3 shows a polypeptide construct comprising a secretion signal, a lipoprotein box, a poly-amino acid linker, a multiple cloning site, and a protein of interest.

FIG. 3 shows another embodiment of the present invention. The hatched box represents the secretion signal and lipoprotein box in a polypeptide construct. In one embodiment of the present invention, a conserved cysteine (C*) is found within the lipoprotein box. This conserved cysteine is acylated by proteins in a host cell, for example Lol proteins in *E. coli*, thereby anchoring the construct to an outer membrane of the host cell. The poly-amino acid linker (dotted box) can begin between preferably between 1 and 30 amino acids, more preferably between 3 and 25 amino acids, and most preferably between 5 and 15 amino acids after the conserved cysteine. In one aspect of the present invention, a multiple cloning site (MCS) is inserted after the poly-amino acid linker. The MCS can be inserted 1 to 100 amino acids, more preferably between 25 and 75 amino acids, and most preferably between 30 and 50 amino acids after the poly-amino acid linker. A protein of interest can be ligated in frame with any one of the secretion signal, lipoprotein box, or poly-amino acid linker, which would allow the protein to be anchored to the outer membrane in its native confirmation. This protein can then be cleaved off the membrane and isolated.

One aspect of the present invention comprises an isolated polypeptide, which further comprises at least two domains. These domains is any one of catalytic domains, binding domains, trans-membrane domains, surface anchoring domains and lipoprotein acylation sites. One domain of the isolated polynucleotide is separated from another domain by a poly-amino acid linker, wherein at least 95% of the amino acids in the poly-amino acid linker are serines. In another aspect of the present invention, at least 90% of the amino acids in the poly-amino acid linker are serines. In another aspect of the present invention, at least 85% of the amino acids in the poly-amino acid linker are serines. In another aspect of the present invention, at least 80% of the amino acids in the poly-amino acid linker are serines. In another aspect of the present invention, at least 75% of the amino acids in the poly-amino acid linker are serines. In another aspect of the present invention, at least 70% of the amino acids in the poly-amino acid linker are serines.

Non-limiting examples of experimental methods used in the present invention are described.

Growth of bacterial strains. *M. degradans* strain 2-40 was grown in minimal medium containing (per liter): 2.3% Instant Ocean, 0.5% ammonium chloride, 0.2% glucose, and 50 mM Tris HCl, pH 7.6. Other carbon sources were added to a final concentration of 0.1%. Agar was added to a final concentration of 1.5% to prepare solid media. All cultures were incubated at 25° C. *E. coli* EC300, DH5αE, and Tuner strains were grown in Luria-Bertani (LB) broth or agar supplemented with the appropriate antibiotics and incubated at 37° C.

Construction of an *M. degradans* strain 2-40 genomic library. Strain 2-40 chromosomal DNA was isolated and prepared for ligation into pCC1. Sau3A fragments of 30 to 40 kb were isolated using gel extraction and ligated into Bam H1H-digested pCC1. The vector was packaged into phage and used to infect *E. coli* EC300. Transductants were selected using chloramphenicol (30 µg/mL).

Screening of the *M. degradans* strain 2-40 genomic library for *chitin depolymerase* activity. *E. coli* transductants were initially screened for *chitin depolymerase* activity by plating the library on LB agar supplemented with 0.1% chitin or 0.08% chitin azure and incubating for 5 days at 37° C. Chitin depolymerase activity was identified by zones of clearing around bacterial colonies. Alternatively, the chitin analogs 4-methylumbelliferyl-β-D-N,N'-diacetylchitobioside (MUF-diNAG) and 4-methylumbelliferyl-β-D-N,N',N"-triacetylchitotrioside (MUF-triNAG) were used to screen transductants for chitinase activity. Single transductants were grown in 100 µL of LB broth supplemented with chloramphenicol (30 µg/mL). Cultures were incubated with gentle shaking at 25° C. for 12 h. A MUF analog was added to a final concentration of 1.5 µM and incubated with shaking at 25° C. for an additional 24 h. Cleavage of the analog was visualized using long-wavelength UV light.

Sodium dodecyl sulfate-polyacrylamide gel electrophoresis (SDS-PAGE) and zymogram analysis. Concentrated culture supernatants of *M. degradans* strain 2-40 were prepared from 50-mL cultures grown at 25° C. for 50 h in minimal medium without glucose and supplemented with 0.1% chitin. All subsequent steps were performed at 4° C. Cultures were centrifuged at 10,000×g for 20 minutes and then sterilized by filtration through a 0.22-µm-pore-size filter. The filter-sterilized supernatant was then concentrated 100-fold using a centrifugal concentrator with a 10-kDa cutoff filter (Millipore). Proteins in concentrated culture supernatants were fractionated by SDSPAGE with a stacking gel in an 8% acrylamide separating gel with a final concentration of 0.01% glycol chitin. Gels were then incubated in refolding buffer (50 mM Tris, 1 mM EDTA, 5 mM 2-mercaptoethanol [pH 7.5]) at 4° C. for 24 h. Gels were washed for 1 h in 100 mM sodium phosphate buffer (pH 7) at 25° C. and then incubated in 100 mM sodium phosphate buffer (pH 7) for 16 h at 37° C. Gels were rinsed and washed in developing buffer (0.5 M Tris, 0.01% Calcofluor [pH 7.5]) for 5 min and then rinsed with distilled water for 2 h with frequent changes of wash water. Zones of chitin depolymerase activity appeared as dark bands when viewed under UV light.

Protein expression and purification. Genes of interest were amplified using PCR and tailed primers. Each gene was digested with the appropriate restriction enzyme, ligated into the pETBlue-2 or pMal-2pX expression vector, and transformed into *E. coli* Tuner or *E. coli* DH5αE cells. A 50-ml culture of transformants carrying the clone of interest was grown at 37° C. to a optical density at 600 nm of 0.5 to 0.6, induced with isopropyl-β-D-thiogalactopyranoside (IPTG), and grown for an additional 3 hours at 37° C. Cells were harvested and resuspended in lysis buffer, and clarified lysates were prepared. pETBlue-2 His tag fusions were bound to Ni-NTA agarose, and pMal-2pX maltose-binding protein (MBP) fusions were purified using amylose resin. Fusion proteins were eluted with imidazole and maltose solutions, respectively. Fractions of interest were concentrated using centrifugal concentrators with 10-kDa cutoff filters, aliquoted, and stored at 80° C.

Chitinase activity assays using chitin analogs and chitooligosaccharides. To determine the specific activities of chitin depolymerases against the chitin analogs MUF-diNAG and MUF-triNAG, 900 μL of a 50 μM solution of each chitin analog was added to 100 μL of purified enzyme and incubated at 37° C. for 30 minutes. The fluorescence of the reaction (excitation wavelength, 365 nm; emitted wavelength, 460 nm) was determined using a Hoefer TKO 100 fluorimeter and compared to a standard curve prepared with 4'-methylumbelliferone. One unit of activity is defined as 1 μmol of 4'-methylumbelliferone released per mg of purified enzyme per min. Products of chitooligosaccharide-modifying enzyme reactions were identified by thin-layer chromatography. Enzyme reaction mixtures contained 0.45 μmol of chitooligosaccharide substrate in 10 mM Tris HCl at pH 7.5. After 1 h at 30° C., reactions were stopped by boiling for 10 minutes. Degradation products were fractionated on silica gel plates, which were developed in 2-propanol:ethanol: distilled water (5:2:1) for 1 hour. The plate was air dried and sprayed with 10% sulfuric acid in ethanol. The plate was dried and baked at 120° C. for 20 min. Chitooligosaccharide spots appeared brown and were compared to standards composed of chitooligosaccharides of known sizes.

DNA and protein sequence manipulations and analyses. Protein modules and domains were identified using the Simple Modular Architecture Tool (SMART) and pFAM database. Similarity searches were performed using the BLAST algorithm at the National Center for Biotechnology Information (NCBI) server. Type II secretion signals were identified using the iPSORT program and the SignalP version 1.1 program. Multiple-sequence alignments were performed using the ClustalW program. Estimated protein molecular masses were calculated using the Peptide Mass Tool at the ExPASy server of the Swiss Institute of Bioinformatics.

Complementation of a nagA mutant. The *M. degradans* strain 2-40 nagA gene was amplified using PCR and tailed primers with 2-40 genomic DNA as the template. The amplified DNA and pBluescript SK+ (Amp$^r$) were digested with the appropriate restriction enzymes and ligated using T4 DNA ligase to create pNagA. *E. coli* K-12 strain IBPC531 (nagA::cm) was transformed with pNagA and plated on GlcNAc-containing minimal medium, which contains M63 minimal salts, 0.2% GlcNAc, ampicillin (50 μg/mL), and chloramphenicol (30 μg/mL).

Cloning and Expression of GH18$_N$ and GH18$_C$. Oligonucleotide primers were designed to amplify the nucleotide sequence corresponding to each catalytic domain by PCR using purified *M. degradans* genomic DNA as a template. Each amplified fragment was then digested with the appropriate restriction enzymes and ligated into the protein expression vector pETBlue2 using T4 DNA ligase. Expression constructs were verified by sequencing and transformed into *E. coli* Tuner™ DE3(pLacI) cells. Protein expression was performed according to standard protocols. Cells were lysed with BugBuster™ NT lysis buffer, centrifuged, and the supernatant collected. Supernatants containing recombinant enzymes were applied to a Ni-NTA agarose column and purified according to the manufacturer's protocol for native protein purification. Purified enzyme samples were quantified using a BSA protein quantification kit.

Glycol chitin zymography. Ethylene glycol chitin was incorporated into the separating portion of an SDS-PAGE gel to a final concentration of 0.01%. After fractionation of the proteins, the zymogram was incubated in refolding buffer (50 mM Tris-Cl, 1 mM EDTA, 5 mM 2-mercaptoethanol, pH 7.5) overnight at 4° C. and subsequently analyzed for chitin depolymerase activity.

Enzyme assays using chitin analogs. Solutions of 4'-methylumbelliferyl-N—N'-diacetylchitobiose [MUF-diNAG] and 4'-methylumbelliferyl-N-N'-N''-triacetylchitotriose [MUF-triNAG] were prepared in 50 mM sodium phosphate buffer (pH 7.0). Reaction mixtures contained 2 μg of purified enzyme and 30 μM analog solution. After incubation for 5 to 10 minutes at 37° C. for GH18$_N$ or 5 to 20 minutes at 30° C. for GH18$_C$ reactions were stopped by submersion in an ice water bath. Liberated methylumbelliferone was detected using a Hoefer TKO-100 fluorimeter. The reaction was measured at multiple time points between 5 and 20 minutes and was found to be linear, with less than 10% of the substrate being degraded.

Oligosaccharide electrophoresis. Reactions of chitooligosaccharides were incubated with 2 volumes of labeling solution (1.0 M sodium cyanoborohydride, 0.2 M 2-aminobenzoic acid) and dried under vacuum. Each sample was mixed with standard 2×SDS-PAGE loading buffer and fractionated in a 15% polyacrylamide gel at 45 mA constant current. Labeled oligosaccharides were visualized under UV light.

Determination of reaction optima for each domain. MUF-diNAG or MUF-triNAG was added to 20 μg of purified enzyme and incubated at a given pH or temperature and activity detected as described above. The buffers used were: sodium acetate (pH 4.0 to 5.5), MES (5.5 to 6.5), PIPES (6.5 to 7.0), HEPES (7.0 to 8.0), and Tris base (8.0 to 9.5). For a given enzyme, reaction conditions that permitted maximum activity were assigned a value of 100%. EDTA, EGTA, KCl, NiCl$_2$, SrCl$_2$, MgCl$_2$, MnCl$_2$, CuCl$_2$, CaCl$_2$, or HgCl$_2$ were added to reaction mixtures to a final concentration of 10 mM; NaCl was added at concentrations up to 1.0 M. Reactions containing metal ions contained 200 μmol enzyme and were incubated for ten minutes at 37° C. for GH18N or twenty minutes at 30° C. for GH18$_C$.

Enzyme assays using chitin and chitin derivatives. Purified enzyme and substrate (2 mg chitin or 10 nmol chitooligosaccharide) were added to 50 mM HEPES, pH 7.5 and incubated at 30° C. The amount of reducing sugar generated was determined by the DNSA assay. Specific enzyme activity was estimated by comparison to a standard curve.

Protein sequence analysis. Analysis of protein domains was performed using the Simple Modular Architecture Research Tool. Similarity between proteins and protein domains was determined by the BLAST algorithm. The lipoprotein anchoring site within ChiB was identified using the Database of Bacterial Lipoproteins.

The nucleotide and protein sequences of ChiA, ChiB, ChiC, CbpA, CdxA, HexA, HexB, and HexC have been placed in GenBank under the accession numbers shown below:

| Gene | Accession No. |
|------|---------------|
| chiA | BK001043 |
| chiB | BK001042 |
| chiC | BK001044 |
| cbpA | BK001045 |
| cdxA | AY233270 |
| hexA | BK001046 |
| hexB | BK001047 |
| hexC | BK001048 |

It is to be understood that while the invention has been described above using specific embodiments, the description and examples are intended to illustrate the structural and functional principles of the present invention and are not intended to limit the scope of the invention. On the contrary, the present invention is intended to encompass all modifications, alterations, and substitutions within the spirit and scope of the appended claims.

What is claimed is:

1. An isolated polypeptide comprising the amino acid sequence of one of SEQ ID NO: 1, SEQ ID NO: 10, and SEQ ID NO: 11.

2. The isolated polypeptide of claim 1, comprising the amino acid sequence of SEQ ID NO:1.

3. The isolated polypeptide of claim 1, comprising the amino acid sequence of SEQ ID NO:10.

4. The isolated polypeptide of claim 1, comprising the amino acid sequence of SEQ ID NO:11.

* * * * *